United States Patent
Rajagopalan et al.

(10) Patent No.: US 9,376,399 B2
(45) Date of Patent: *Jun. 28, 2016

(54) FLUORESCENT PYRAZINE DERIVATIVES AND METHODS OF USING THE SAME IN ASSESSING RENAL FUNCTION

(71) Applicant: MediBeacon, LLC, St. Louis, MO (US)

(72) Inventors: Raghavan Rajagopalan, Solon, OH (US); Richard B. Dorshow, St. Louis, MO (US); William L. Neumann, St. Louis, MO (US); Dennis A. Moore, St. Louis, MO (US)

(73) Assignee: MediBeacon LLC, St. Louis, MO (US)

( * ) Notice: Subject to any disclaimer, the term of this patent is extended or adjusted under 35 U.S.C. 154(b) by 22 days.

This patent is subject to a terminal disclaimer.

(21) Appl. No.: 14/047,733

(22) Filed: Oct. 7, 2013

(65) Prior Publication Data
US 2014/0039191 A1    Feb. 6, 2014

Related U.S. Application Data

(62) Division of application No. 11/721,186, filed as application No. PCT/US2005/046732 on Dec. 22, 2005, now Pat. No. 8,778,309.

(60) Provisional application No. 60/638,611, filed on Dec. 23, 2004.

(51) Int. Cl.
| | |
|---|---|
| C07D 241/28 | (2006.01) |
| C07D 241/20 | (2006.01) |
| C07D 241/26 | (2006.01) |
| A61K 31/4965 | (2006.01) |
| A61K 49/00 | (2006.01) |

(52) U.S. Cl.
CPC .......... *C07D 241/28* (2013.01); *A61K 31/4965* (2013.01); *A61K 49/0004* (2013.01); *A61K 49/0021* (2013.01); *A61K 49/0052* (2013.01); *C07D 241/20* (2013.01); *C07D 241/26* (2013.01)

(58) Field of Classification Search
None
See application file for complete search history.

(56) References Cited

U.S. PATENT DOCUMENTS

| | | | |
|---|---|---|---|
| 3,808,209 A | 4/1974 | Donald | |
| 3,814,757 A | 6/1974 | Donald | |
| 3,948,895 A | 4/1976 | Donald | |
| 4,517,186 A | 5/1985 | Johnston | |
| 6,440,389 B1 | 8/2002 | Rabito | |
| 2004/0081622 A1 | 4/2004 | Achilefu et al. | |

FOREIGN PATENT DOCUMENTS

| | | |
|---|---|---|
| EP | 0402472 | 12/1990 |
| EP | 0579835 A1 | 1/1994 |
| JP | 2017163 | 1/1990 |
| JP | 249775 | 2/1990 |
| JP | 4112877 | 4/1992 |
| JP | 07149736 | 6/1995 |
| JP | 07278456 | 10/1995 |
| JP | 1997143168 A | 12/1995 |
| JP | 1997202765 A | 8/1997 |
| JP | 09249773 | 9/1997 |
| JP | 10045727 | 2/1998 |
| JP | 1998045727 | 2/1998 |
| JP | 1999092462 | 4/1999 |
| WO | 88/01264 | 2/1988 |
| WO | 91/08510 | 6/1991 |
| WO | 00/10983 | 3/2000 |

OTHER PUBLICATIONS

Shirai et al. 1998 Dyes and Pigments 39: 49-68.*
Yudin et al. Facile synthesis of polyhalo- and nitro-pyrazines. 1995 Mendeleev Communications 5: 196-197.*
Philbin et al. Preparation of 2,5-diamino-3,6-dinitropyrazine (ANPZ-i): a novel candidate high energy insensitive explosive. 2000 Propellants, Explosives, Pyrotechnics 25: 302-306.*
Pfleiderer W. 230: Wolfgang Pfleiderer: Ein Beitrag zum Mechanismus der Kondensation von o-Diaminen mit Alloxan and Dimethyl-alloxan. Jul. 11, 1955, DD. English translation of Title, Abstract, and 3rd paragraph and compounds XIII and XIV of p. 1629.*
Baker et al., Epidemiology of trauma deaths, The American Journal of Surgery, vol. 40, Issue 1, Jul. 1980, 144-150.
Barlin, G.B., The pyrazines. In the Chemistry of Heterocyclic Compounds., Weissberger and Taylor, Editors, John Wiley & Sons, New York: 1982, 205-246.

(Continued)

*Primary Examiner* — Michael G Hartley
*Assistant Examiner* — Jennifer Lamberski
(74) *Attorney, Agent, or Firm* — Dennis A. Bennett; Brock Levin

(57) ABSTRACT

The present invention relates to pyrazine derivatives such as those represented by Formulas I and II. $X^1$ to $X^4$ of Formulas I and II may be characterized as electron withdrawing groups, while $Y^1$ to $Y^4$ of Formulas I and II may be characterized as electron donating groups. Pyrazine derivatives of the present invention may be utilized in assessing organ (e.g., kidney) function.

8 Claims, 8 Drawing Sheets

Formula I

Formula II

(56) References Cited

OTHER PUBLICATIONS

Cerra, Multiple Organ Failure Syndrome, In New Horizons: Multiple Organ Failure, Bihari and Cerra, (eds) Fullerton, CA, 1989, 1-24.

Choyke et al., Hydrated clearance of gadolinium-DTPA as a measurement of glomerular filtration rate, Kidney International, 1992, 41, 1595-1598.

Coalson, Pathology of Sepsis, Septic Shock, and Multiple Organ Failure, IriNew Horizons: Multiple Organ Failure, Bihari and Cerra, (eds), Society of Critical Care Medicine, Fullerton, CA, 1986, 27-59.

Dollan et al., A clinical appraisal of the plasma concentration and endogenous clearance of creatintine, American Journal of Medicine, 1962, 32, 65-79.

Dorshow et al., Monitoring Physiological Function by Detection of Exogenous Fluorescent Contrast Agents., Optical Diagnostics of Biological Fluids IV, Priezzhev & Asakura Editors, Proceedings of SPIE, 1999, 3599, 2-8.

Dorshow et al., Non-Invasive Fluorescence Detection of Hepatic and Renal Function, Bull. Am. Phys. Soc., 1997, 42, 681.

Dorshow et al., "Non-invasive fluorescence detection of physiological function", Part of the SPIE Conference on Optical diagniostics of Biological Fluids 111, San Jose, California, Jan. 28-29, 1998, vol. 3252, pp. 124-130.

Dorshow et al., Noninvasive renal function assessment by fluorescence detection, Biomedical Optical Spectroscopy and Diagnostics, Trends in Optics and Photonics Series 22, Sevick-Muraca, Izatt, and Ediger Eidtors, Octical Society of America, Washington D.C., 1998, 54-56.

Ekanoyan et al., In Clinical Practice Guidelines for Chronic Kidney Disease: Evaluation, Classification, and Stratification (K/DOQI). National Kidney Foundation: Washington, D.C., 2002, 1-22.

Fritzberg et al., Synthesis and biological evaluation of technetium-99m MAG3 as a hippuran replacement, J. Nucl. Med., 1986, 27, 111-116.

Guesry et al., Measurement of giomerular filtration rate by fluorescent excitation of non-radioactive meqlumine iothalamate., Clinical Nephroloqv, 1975, 3, 134-138.

Henry Edition, {Ed.), Clinical Diagnosis and Management by Laboratory Methods, 215 Edition, WB Saunders, Philadelphia, PA, 1984, Chapter 8 76-90, Chapter 14 147-169.

Hartman et al.. "Synthesis and Reactions of 5,6-Dichloro-3-nitropyrazinamine", Jul.-Aug. 1983, J. Heterocyclic chem.., 20, PD. 1089-1091.

Kaminsky et al., Some congeners and Analogs of Dipyridamole, Journal Med. Chem., Jul. 1996, 9, 610-612.

Kim et al., Self-assembling of aminopyrazine fluorescent dyes and their solid state spectra., Dyes and Pioments, 1998, 39(4), 341-357.

Kim et al., Dyes & Pigments, 1999, vol. 41, 183-191.

Lewis et al., Comparative evaluation of urographic contrast media, inulin, and mTc-DTPA clearance methods for determination of glomerular filtration rate in clinical transplantation, Transplantation, 1989, 48, 790-796.

Author is Regel, Treatment results of patients with multiple trauma: an analysis of 3406 cases treated Between 1972 and 1991 at a German Level I Trauma Center, Journal of Trauma, 1995, 38, 70-77.

Lundqvist et al., Iohexol clearance for renal function measurement in gynaecologic cancer patients., Acta Radiol., 1996, Jul., 37(4):582-586.

Muller et al., Medical Optical Tomography, SPIE vol. IS11, 1993, 553-588.

Mulle-Sour et al., Glomerular filtration and tubular secretion of MAG3 in rat kidney, Journal of Nuclear Medicine, 1989, 30, 1986-1991.

Nally Jr., Acute renal failure in hospitalized patients, Cleveland Clinic Journal of Medicine, 2002, 69(7), 569-574.

Nosco et al., Chemistry of technetium radiopharmaceuticals 1: Chemistry behind the development of technetium-99m compounds to determine kidney function, Coordination Chemistry Reviews, 1999, 184, 91-123.

Ozaki, et al., Sensitization of europium(III) luminescence by DTPA derivatives, Chemistry Letters, 2000, 312-313.

Perchais et al., Carboacides Polycyanes-V Preparation Et Proprietes Des Sels D'Aza-2 Propenures Polycyanes, Tetrahedron, 1974, vol. 30, No. 8, English abstract only.

Philbin et al., Preparation of 2,5-Diamino-3,6-Dinitropyrazine (ANPZ-i): A Novel Candidate High Energy Insensitive Explosive, Propellants, Explosives, Pyrotechnics 25, 2000, 302-306.

Rabito et al., Renal function in patients at risk of contrast material-induced acute renal failure: noninvasive, real-time monitoring, Radiology, 1993, 186:851-854.

Rajagopalan et al., Polyionic fluorescent bioconjugates as composition agents for continuous monitoring of renal function, Molecular Imaging: Reporters, Dyes, Markers, and Instrumentation, Priezzhev, Asakura, and Briers Editors, Proceedings of SPIE, 2000, 3924.

Roch-Ramel et al.. Renal excretion and tubular transport of organic anions and cations, In Handbook of Physiology, Section 8, NeuroloQical PhvsioloQY, 1992, vol. II, EE, 189-262.

Sato, Studies on Pyrazines. 24[1]. A Simple and Versatile Synthetic Method for 3-Alkozy-and 3- Aminoovrizinecarbonitriles, Heterovcvclic Chem., 1992, 29(7), DD. 1689-1692.

Sato, "Product clas 14: pyrazines", 2004, 16, pp. 751-844, Science of Synthesis: Houben-Weyl Methods of Molecular Transformations.

Sekar, Pyrazine dyes: An Update, Colourage, Jan. 1999, 41, 42, 44.

Shafei et al., "Synthesis and reactions of some pyrazine derivatives", Synthetic Communications, 1994, 24(13), pp. 1895-1916.

Shirai et al., Synthesis and fluorescent properties of 2,5-diamino-3,6-dicyanopyrazine dyes., Dyes and Pioments, 1998, 39(1), 49-68.

Sohtell et al., FITC-inulin as a kidney tubule marker in the rat, Acta Physiol Scand, 1983, 119, 313-316.

Taylor et al., Pyrimidopteridines by Oxidative Self-condensation of Aminopyrimidines, Contribution from the Notes Chemical Laboratory, University of Illinois, and the Welcome Research Laboratories, Apr. 20, 1955, vol. 77, 2243-2248.

Tauxe, Tubular Function. In Nuclear Medicine in Clinical Urology and Nephrology, Tauxe and Dubovsky (Eds.), Accleton Century Crofts: East Norwalk, 1985, 77-105.

Tilney et al., Acute renal failure in surgical patients: Causes, clinical patterns, and care., Surgical Clinics of North America, 1983, 63, 357-377.

Vanzee et al., Renal injury associated with intravenous pyelography in nondiabetic and diabetic patients., Ann Intern Med., Jul. 1978, 89(1):51-54.

Wang et al., "Design of novel nonlinear optical chromophores with multiple substitutions", Phys. Chem. Chem. Phys., 1999, 1, PD. 3519-3525.

Zhang et al., "A regioselective synthesis of methyl 7-amino-3-phenylthieno [2m3-b]pyrazine-6- carboxvlate", Synthetic Communications, 2001, 32(5), DD. 725-730.

* cited by examiner

PRIOR ART
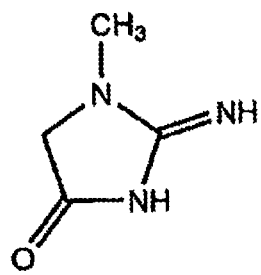
Creatinine (1)
MW: 113
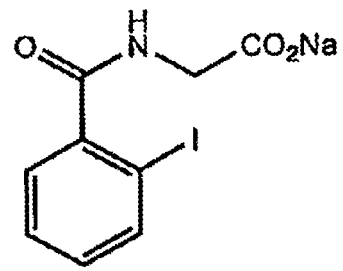
o-Iodohippurate (2)
MW: 327
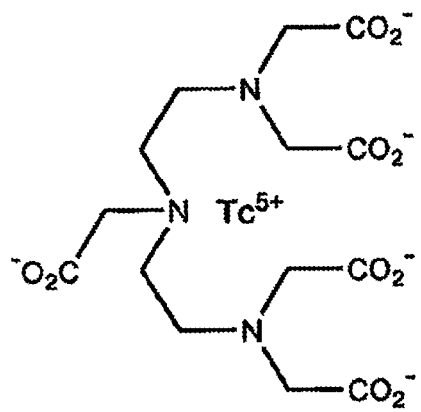
$^{99m}$Tc-DTPA (3)
MW: 487
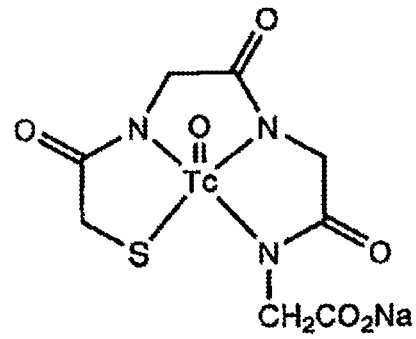
$^{99m}$Tc-MAG3 (4)
MW: 364
Fig. 1

PRIOR ART
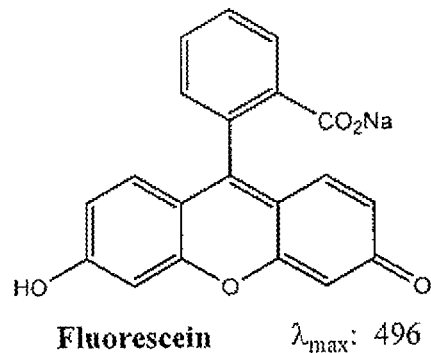
Fluorescein  $\lambda_{max}$: 496
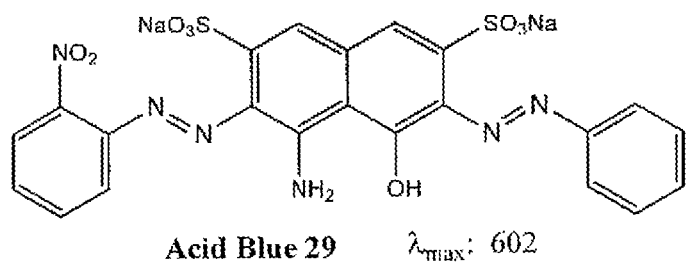
Acid Blue 29  $\lambda_{max}$: 602
Fig. 2
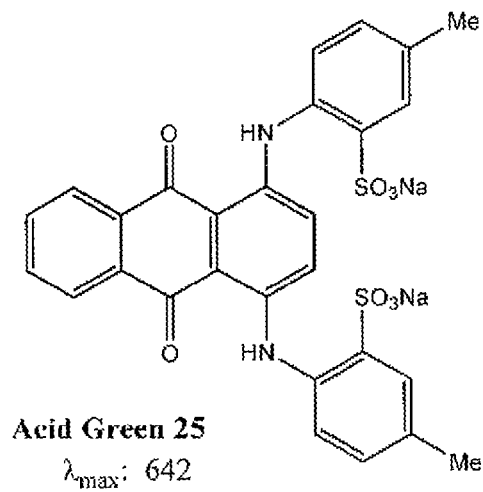
Acid Green 25
$\lambda_{max}$: 642
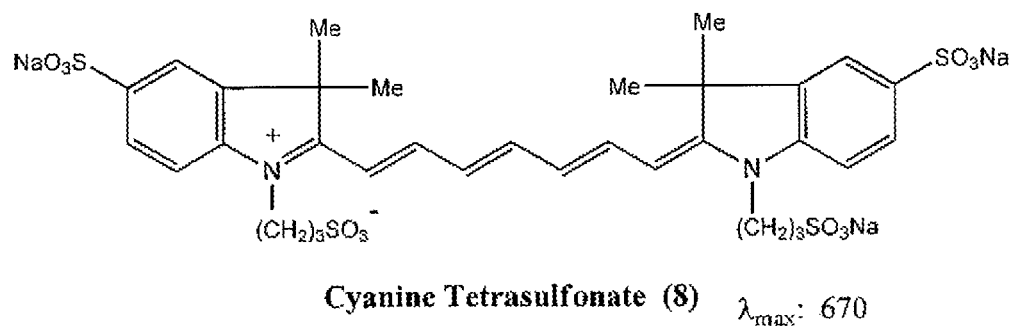
Cyanine Tetrasulfonate (8)  $\lambda_{max}$: 670

FLUORESCENT PYRAZINE DERIVATIVES AND METHODS OF USING THE SAME IN ASSESSING RENAL FUNCTION

This application is a Divisional of U.S. application Ser. No. 11/721,186 filed Jun. 8, 2007, which is a National Stage of International Application Ser. No. PCT/US2005/046732 filed Dec. 22, 2005 that claims priority from U.S. Provisional Application 60/638,611, filed Dec. 23, 2004, each of which is incorporated herein by reference.

FIELD OF THE INVENTION

The present invention relates to pyrazine derivatives that may be characterized as hydrophilic, small molecule dyes capable of absorbing and/or emanating spectral energy in the visible and/or near infrared spectrum. In addition, the present invention relates to methods of using pyrazine derivatives in the monitoring of renal function.

BACKGROUND

Acute renal failure (ARF) is a common ailment in patients admitted to general medical-surgical hospitals. Approximately half of the patients who develop ARF die, and survivors face marked increases in morbidity and prolonged hospitalization [1]. Early diagnosis is generally believed to be critical, because renal failure is often asymptomatic and typically requires careful tracking of renal function markers in the blood. Dynamic monitoring of renal function of patients is highly desirable in order to minimize the risk of acute renal failure brought about by various clinical, physiological and pathological conditions [2-6]. Such dynamic monitoring is particularly important in the case of critically ill or injured patients, because a large percentage of these patients tend to face the risk of multiple organ failure (MOF) potentially resulting in death [7, 8]. MOF is a sequential failure of the lungs, liver and kidneys and is incited by one or more of acute lung injury (ALI), adult respiratory distress syndrome (ARDS), hypermetabolism, hypotension, persistent inflammatory focus and sepsis syndrome. The common histological features of hypotension and shock leading to MOF generally include tissue necrosis, vascular congestion, interstitial and cellular edema, hemorrhage and microthrombi. These changes generally affect the lungs, liver, kidneys, intestine, adrenal glands, brain and pancreas in descending order of frequency [9]. The transition from early stages of trauma to clinical MOF generally corresponds with a particular degree of liver and renal failure as well as a change in mortality risk from about 30% up to about 50% [10].

Traditionally, renal function of a patient has been determined using crude measurements of the patient's urine output and plasma creatinine levels [11-13]. These values are frequently misleading because such values are affected by age, state of hydration, renal perfusion, muscle mass, dietary intake, and many other clinical and anthropometric variables. In addition, a single value obtained several hours after sampling is difficult to correlate with other important physiologic events such as blood pressure, cardiac output, state of hydration and other specific clinical events (e.g., hemorrhage, bacteremia, ventilator settings and others).

With regard to conventional renal monitoring procedures, an approximation of a patient's glomerular filtration rate (GFR) can be made via a 24 hour urine collection procedure that (as the name suggests) typically requires about 24 hours for urine collection, several more hours for analysis, and a meticulous bedside collection technique. Unfortunately, the undesirably late timing and significant duration of this conventional procedure can reduce the likelihood of effectively treating the patient and/or saving the kidney(s). As a further drawback to this type of procedure, repeat data tends to be equally as cumbersome to obtain as the originally acquired data.

Occasionally, changes in serum creatinine of a patient must be adjusted based on measurement values such as the patient's urinary electrolytes and osmolality as well as derived calculations such as "renal failure index" and/or "fractional excretion of sodium." Such adjustments of serum creatinine undesirably tend to require contemporaneous collection of additional samples of serum and urine and, after some delay, further calculations. Frequently, dosing of medication is adjusted for renal function and thus can be equally as inaccurate, equally delayed, and as difficult to reassess as the measurement values and calculations upon which the dosing is based. Finally, clinical decisions in the critically ill population are often equally as important in their timing as they are in their accuracy.

Thus, there is a need to develop improved compositions, devices and methods for measuring renal function (e.g., GFR) using non-ionizing radiation. The availability of a real-time, accurate, repeatable measure of renal excretion rate using exogenous markers under a variety of circumstances would represent a substantial improvement over any currently available or widely practiced method. Moreover, since such an invention would depend heavily on the renal elimination of the exogenous marker(s), the measurement would ideally be absolute and would, thus, preferably require little or no subjective interpretation based on age, muscle mass, blood pressure and the like. Indeed, such an invention would enable assessment of renal function under particular circumstances at particular moments in time.

It is known that hydrophilic, anionic substances are generally capable of being excreted by the kidneys [14]. Renal clearance typically occurs via two pathways: glomerular filtration and tubular secretion. Tubular secretion may be characterized as an active transport process, and hence, the substances clearing via this pathway typically exhibit specific properties with respect to size, charge and lipophilicity.

Most of the substances that pass through the kidneys are filtered through the glomerulus (a small intertwined group of capillaries in the malpighian body of the kidney). Examples of exogenous substances capable of clearing the kidney via glomerular filtration (hereinafter referred to as "GFR agents") are shown in FIG. 1 and include creatinine (1), o-iodohippuran (2), and $^{99m}$Tc-DTPA (3) [15-17]. Examples of exogenous substance that is capable of undergoing renal clearance via tubular secretion include $^{99m}$Tc-MAG3 (4) and other substances known in the art [15, 18, 19]. $^{99m}$Tc-MAG3 (4) is also widely used to assess renal function through gamma scintigraphy as well as through renal blood flow measurement. As one drawback to the substances illustrated in FIG. 1, o-iodohippuran (2), $^{99m}$Tc-DTPA (3) and $^{99m}$Tc-MAG3 (4) include radioisotopes to enable the same to be detected. Even if non-radioactive analogs (e.g., such as an analog of o-iodohippuran (2)) or other non-radioactive substances were to be used for renal function monitoring, such monitoring would require the use of undesirable ultraviolet radiation for excitation of those substances.

Currently, no reliable, continuous, repeatable method for the assessment of specific renal function using a non-radioactive, exogenous renal agent is commercially available. Among the non-radioactive methods, fluorescence measurement tends to offer the greatest sensitivity. In principle, there are two general approaches for designing fluorescent renal agents. The first approach would involve enhancing the fluorescence of known renal agents that are intrinsically poor emitters (e.g. lanthanide metal complexes) [21, 22], and the second approach would involve transforming highly fluorescent dyes (which are intrinsically lipophilic) into hydrophilic, anionic species to force them to clear via the kidneys.

Accordingly, it would be quite desirable to transform highly fluorescent dyes into hydrophilic, anionic species. More particularly, it would be quite desirable to identify appropriate, small, fluorescent molecules and render such molecules hydrophilic. Examples of dyes capable of absorbing light in the visible and/or NIR regions are shown in FIG. 2. These dyes are often relatively large in size, contain multiple aromatic rings, and are highly lipophilic compared to the structures shown in FIG. 1. Large lipophilic molecules almost always clear via the hepatobiliary system and do not readily clear via renal pathways. For example, FIG. 3 shows that tetrasulfonated cyanine dye (8 of FIG. 2) exhibits a poor rate of clearance from the blood. In attempts to circumvent this problem, some dyes have been conjugated to polyanionic carriers [23, 24]. Although these dye-polymer conjugates generally possess acceptable renal clearance properties, such polymeric compounds have other drawbacks such as polydispersity, manufacturing and quality control issues, and the provocation of undesired immune responses that may preclude their use as diagnostic and/or therapeutic substances. Accordingly, development of small, hydrophilic dyes is quite desirable to enable enhanced measurement of renal functioning and clearance.

SUMMARY

The present invention generally relates to the transformation of fluorescent dyes into hydrophilic and/or anionic species by substituting both electron withdrawing and electron donating substituents (i.e., one or more of each) to the dyes. For example, one aspect of the present invention is directed to rigid, small molecules whose size is preferably similar to that of creatinine or o-iodohippuran and rendering such molecules hydrophilic by incorporating appropriate polar functionalities such as hydroxyl, carboxyl, sulfonate, phosphonate and the like into their backbones. Incidentally, the "backbone" of a molecule is a term that is frequently used in the art to designate a central portion or core of the molecular structure. For the purpose of this invention, a "small molecule" is an aromatic or a heteroaromatic compound: (1) that exhibits a molecular weight less than about 500 Daltons; (2) that is capable of absorbing spectral energy of at least about 400 nm (e.g., visible and/or near infrared light); and (3) that is capable of emanating spectral energy of at least about 400 nm (e.g., visible and/or near infrared light). Further, a "rigid" molecule refers to a molecule that undergoes little, if any, internal rotational movement. Pyrazine derivatives of the invention may be desirable for renal applications because they tend to be cleared from the body via the kidneys, may demonstrate strong absorption and/or emission/fluorescence in the visible region, and tend to exhibit significant Stokes shifts. These properties allow great flexibility in both tuning the molecule to the desired wavelength and introducing a wide variety of substituents to improve clearance properties.

In a first aspect, the present invention is directed to pyrazine derivatives of Formula I (below). With regard to Formula I, $X^1$ and $X^2$ may, at least in some embodiments, be characterized as electron withdrawing substituents, and each may independently chosen from the group consisting of —CN, —CO$_2$R$^1$, —CONR$^2$R$^3$, —COR$^4$, —NO$_2$, —SOR$^5$, —SO$_2$R$^6$, —SO$_3$OR$^7$ and —PO$_3$R$^8$R$^9$. Further, $Y^1$ and $Y^2$ may, at least in some embodiments, be characterized as electron donating substituents and may be independently chosen from the group consisting of —OR$^{10}$, —SR$^{11}$, —NR$^{12}$R$^{13}$, —N(R$^{14}$)COR$^{15}$ and substituents corresponding to Formula A below. $Z^1$ may be a direct bond, —CR$^{16}$R$^{17}$—, —O—, —NR$^{18}$—, —NCOR$^{19}$—, —S—, —SO— or —SO$_2$—. "m" and "n" may independently be any appropriate integers. For instance, in some embodiments, each of "m" and "n" may independently be between 1 and 6 (inclusive). As another example, in some embodiments, each of "m" and "n" may independently be between 1 and 3 (inclusive). R$^1$ to R$^{19}$ may be any suitable substituents capable of enhancing biological and/or physicochemical properties of pyrazine derivatives of Formula I. For example, for renal function assessment, each of the R groups of R$^1$ to R$^{19}$ may independently be any one of a hydrogen atom, an anionic functional group (e.g., carboxylate, sulfonate, sulfate, phopshonate and phosphate) and a hydrophilic functional group (e.g., hydroxyl, carboxyl, sulfonyl, sulfonato and phosphonato).

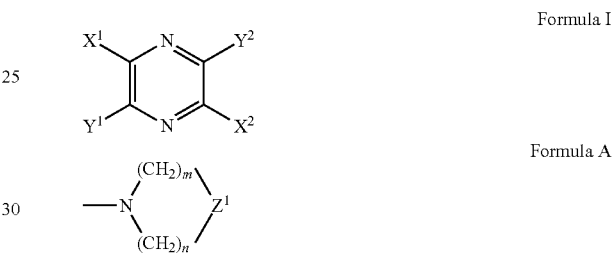

Formula I

Formula A

A second aspect of the invention is directed to pyrazine derivatives of Formula II. With regard to Formula II, $X^3$ and $X^4$ may, at least in some embodiments, be characterized as electron withdrawing substituents and may be independently chosen from the group consisting of —CN, —CO$_2$R$^{20}$, —CONR$^{21}$R$^{22}$, —COR$^{23}$, —NO$_2$, —SOR$^{24}$, —SO$_2$R$^{25}$, —SO$_2$OR$^{26}$ and —PO$_3$R$^{27}$R$^{28}$. By contrast, $Y^3$ and $Y^4$ may, at least in some embodiments, be characterized as electron donating substituents and may be independently chosen from the group consisting of —OR$^{29}$, —SR$^{30}$, —NR$^{31}$R$^{32}$, —N(R$^{32}$)COR$^{34}$ and substituents corresponding to Formula B below. $Z^2$ is preferably a direct bond, —CR$^{35}$R$^{36}$—, —O—, —NR$^{37}$—, —NCOR$^{38}$, —S—, —SO— or —SO$_2$—. "p" and "q" may independently be any appropriate integers. For instance, in some embodiments, each of "p" and "q" may independently be between 1 and 6 (inclusive). As another example, in some embodiments, each of "p" and "q" may independently be between 1 and 3 (inclusive). R$^{20}$ to R$^{38}$ may be any appropriate substituents capable of enhancing biological and/or physicochemical properties of pyrazine derivatives of Formula II. For example, for renal function assessment, each of the R groups of R$^{20}$ to R$^{38}$ may independently be any one of a hydrogen atom, an anionic functional group (e.g., carboxylate, sulfonate, sulfate, phopshonate and phosphate) and a hydrophilic functional group (e.g., hydroxyl, carboxyl, sulfonyl, sulfonato and phosphonato).

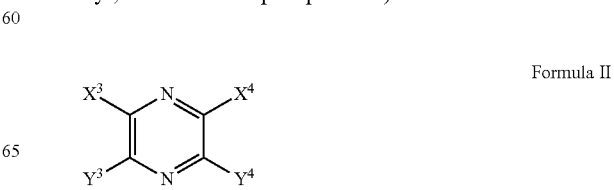

Formula II

-continued

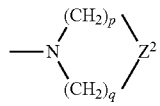

Formula B

Yet a third aspect of the invention is directed to methods of determining renal function using pyrazine derivatives such as those described above with regard to Formulas I and II. In these methods, an effective amount of a pyrazine derivative is administered into the body of a patient (e.g., a mammal such as a human or animal subject). Incidentally, an "effective amount" herein generally refers to an amount of pyrazine derivative that is sufficient to enable renal clearance to be analyzed. The composition is exposed to at least one of visible and near infrared light. Due to this exposure of the composition to the visible and/or infrared light, the composition emanates spectral energy that may be detected by appropriate detection equipment. This spectral energy emanating from the composition may be detected using an appropriate detection mechanism such as an invasive or non-invasive optical probe. Herein, "emanating" or the like refers to spectral energy that is emitted and/or fluoresced from a composition of the invention. Renal function can be determined based the spectral energy that is detected. For example, an initial amount of the amount of composition present in the body of a patient may be determined by a magnitude/intensity of light emanated from the composition that is detected (e.g., in the bloodstream). As the composition is cleared from the body, the magnitude/intensity of detected light generally diminishes. Accordingly, a rate at which this magnitude of detected light diminishes may be correlated to a renal clearance rate of the patient. This detection may be done periodically or in substantially real time (providing a substantially continuous monitoring of renal function). Indeed, methods of the present invention enable renal function/clearance to be determined via detecting a change and/or a rate of change of the detected magnitude of spectral energy (indicative of an amount of the composition that has not been cleared) from the portion of the composition that remains in the body.

Yet a fourth aspect of the invention is directed to methods for preparing 2,5-diaminopyrazine-3,6-dicarboxylic acid. In these methods, a hydrolysis mixture including 2,4,6,8-tetrahydroxypyrimido(4,5-g)pteridine or a salt thereof is irradiated with microwaves.

BRIEF DESCRIPTION OF THE FIGURES

FIG. 1: Structures of small molecule renal agents.
FIG. 2: Structures of conventional visible and NIR dyes.
FIG. 8A is a projection view of the molecule with 50% thermal ellipsoids and FIG. 8B is projection view of the molecule with 50% thermal ellipsoids and coordination sphere of the Na atoms.

DETAILED DESCRIPTION OF VARIOUS EMBODIMENTS

Figure 3:
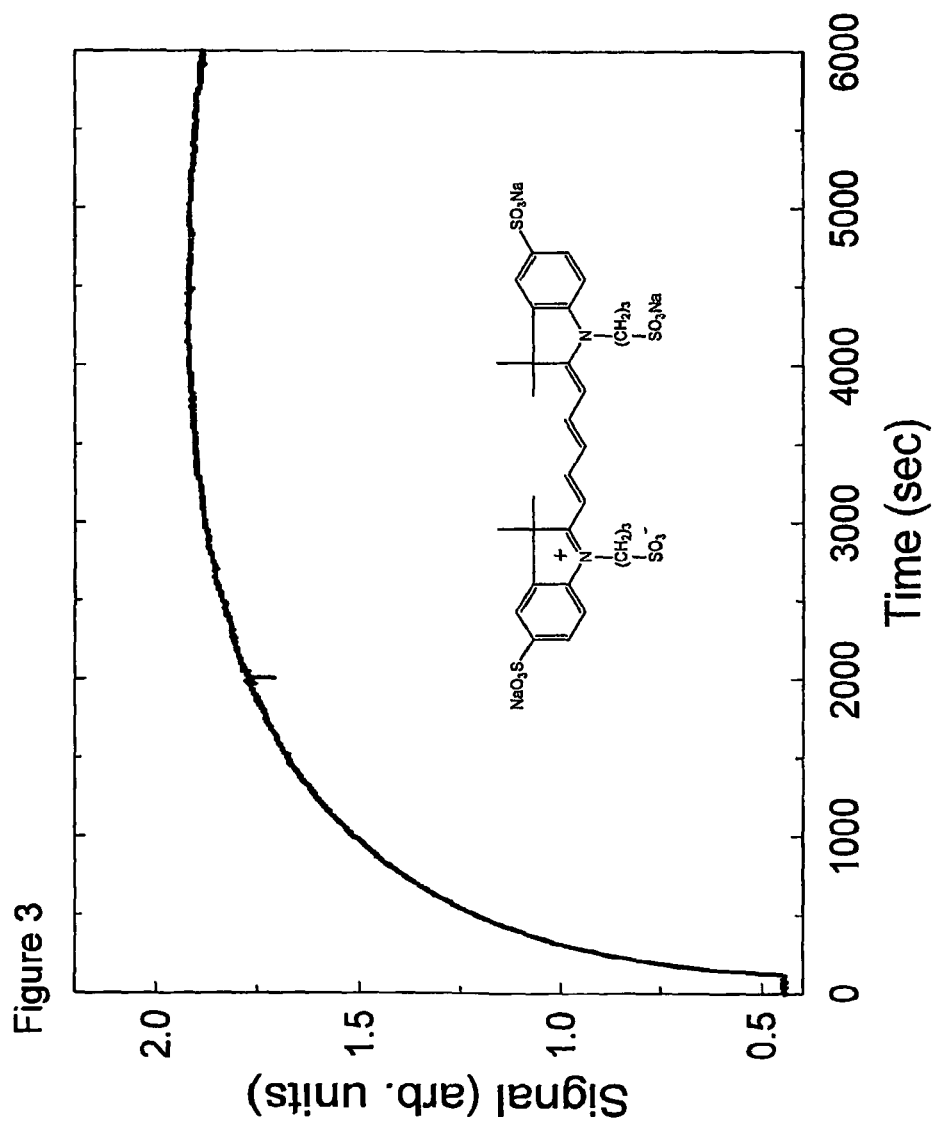
FIG. 3: Blood clearance profile of cyanine tetrasulfonate dye (8).

The present invention discloses renal function monitoring compounds. An example of a particular compound of the invention corresponds to Formula I below. In this exemplary embodiment, $X^1$ and $X^2$ are electron withdrawing substituents independently chosen from the group consisting of —CN, —$CO_2R^1$, —$CONR^2R^3$, —$COR^4$, —$NO_2$, —$SOR^5$, —$SO_2R^6$, —$SO_2OR^7$ and —$PO_3R^8R^9$. $Y^1$ and $Y^2$ are independently chosen from the group consisting of —$OR^{10}$, —$SR^{11}$, —$NR^{12}R^{13}$, —$N(R^{14})COR^{15}$ and substituents represented by Formula A. $Z^1$ is selected from the group consisting of a direct bond, —$CR^{16}R^{17}$—, —O—, —$NR^{18}$—, —$NCOR^{19}$—, —S—, —SO— and —$SO_2$—. Each of the R groups of $R^1$ to $R^{19}$ are independently selected from the group consisting of hydrogen, C3-C6 polyhydroxylated alkyl, —(($CH_2)_2$—O—($CH_2)_2$—O$)_a$—$R^{40}$, C1-C10 alkyl, C5-C10 aryl, C5-C10 heteroaryl, —$(CH_2)_a$OH, —$(CH_2)_a$$CO_2$H, —$(CH_2)_a$$SO_3$H, —$(CH_2)_a$$SO_3^-$, —$(CH_2)_a$$OSO_3$H, —$(CH_2)_a$$OSO_3^-$, —$(CH_2)_a$$NHSO_3$H, —$(CH_2)_a$$NHSO_3^-$, —$(CH_2)_a$$PO_3H_2$, —$(CH_2)_a$$PO_3$H$^-$, —$(CH_2)_a$$PO_3^-$, —$(CH_2)_a$$OPO_3H_2$, —$(CH_2)_a$$OPO_3$H$^-$ and —$(CH_2)_a$$OPO_3$. $R^{40}$ is selected from the group consisting of hydrogen, C1-C10 alkyl, C5-C10 aryl, C5-C10 heteroaryl, —$(CH_2)_a$OH, —$(CH_2)_a$$CO_2$H, —$(CH_2)_a$$SO_3$H, —$(CH_2)_a$$SO_3^-$, —$(CH_2)_a$$OSO_3$H, —$(CH_2)_a$$OSO_3^-$, —$(CH_2)_a$$NHSO_3$H, —$(CH_2)_a$$NHSO_3^-$, —$(CH_2)_a$$PO_3H_2$, —$(CH_2)_a$$PO_3^-$, —$(CH_2)_a$$PO_3^-$, —$(CH_2)_a$$OPO_3H_2$, —$(CH_2)_a$$OPO_3$H$^-$ and —$(CH_2)_a$$OPO_3$. "m" and "n" independently fall within the range of 1 to 6 inclusive in some embodiments, and independently fall within the range of 1 to 3 inclusive in some embodiments. "a" is an integer from 1 to 10 inclusive in some embodiments, and is an integer from 1 to 6 inclusive in some embodiments.

In some embodiments represented by Formula I, each of $X^1$ and $X^2$ are —CN, —$CO_2R^1$ or —$CONR^2R^3$, each of $Y^1$ and $Y^2$ are —$NR^{12}R^{13}$ or the substituent of Formula A, and $Z^1$ is a direct bond. In such compositions, each of $R^1$, $R^2$, $R^3$, $R^{12}$ and $R^{13}$ is not hydrogen, C1-C10 alkyl or C1-C10 aryl, and m, n, N and $Z^1$ together do not form a 5- or 6-membered ring.

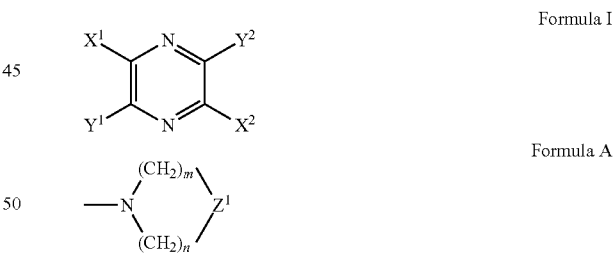

Formula I

Formula A

In some embodiments represented by Formula I, $X^1$ and $X^2$ are independently selected from the group consisting of —CN, —$CO_2R^1$, —$CONR^2R^3$, —$SO_2R^6$ and —$SO_2OR^7$. Further, $Y^1$ and $Y^2$ are independently selected from the group consisting of —$NR^{12}R^{13}$, —$N(R^{14})COR^{15}$ and substituents represented by Formula A. $Z^1$ is selected from the group consisting of a direct bond, —$CR^{16}R^{17}$—, —O—, —$NR^{18}$—, —$NCOR^{19}$—, —S—, —SO— and —$SO_2$—. The R groups of $R^1$ to $R^{19}$ are each independently selected from the group consisting of hydrogen, C3-C6 polyhydroxylated alkyl, —(($CH_2)_2$—O—($CH_2)_2$—O$)_a$—$R^{40}$, C1-C10 alkyl, C5-C10 heteroaryl, C5-C10 aryl, —$(CH_2)_a$OH, —$(CH_2)_a$$CO_2$H, —$(CH_2)_a$$SO_3$H and —$(CH_2)$$SO_3^-$. Further; "a", "m" and "n" fall within a range from 1 to 3 inclusive.

In some embodiments represented by Formula I, $X^1$ and $X^2$ are independently chosen from the group consisting of —CN, —$CO_2R^1$ and —$CONR^2R^3$. $Y^1$ and $Y^2$ are independently selected from the group consisting of —$NR^{12}R^{13}$ and substituents represented by Formula A. $Z^1$ is selected from the group consisting of a direct bond, —$CR^{16}R^{17}$—, —O—, —$NR^{18}$—, —$NCOR^{19}$—, —S—, —SO— and —$SO_2$—. Each of the R groups of $R^1$ to $R^{19}$ is independently selected from the group consisting of hydrogen, C3-C6 polyhydroxylated alkyl, —$((CH_2)_2$—O—$(CH_2)_2$—O$)_a$—$R^{40}$, C1-C10 alkyl, —$(CH_2)_a$OH and —$(CH_2)CO_2H$. Further, "a," "m" and "n" are within a range from 1 to 3 inclusive.

Another example of a particular compound of the invention corresponds to Formula II below. In this exemplary embodiment, $X^3$ and $X^4$ are electron withdrawing substituents independently selected from the group consisting of —CN, —$CO_2R^{20}$, —$CONR^{21}R^{22}$, —$COR^{23}$, —$NO_2$, —$SOR^{24}$, —$SO_2R^{25}$, —$SO_2OR^{26}$ and —$PO_3R^{27}R^{28}$. $Y^3$ and $Y^4$ are electron donating substituents independently selected from the group consisting of —$OR^{29}$, —$SR^{30}$, —$NR^{31}R^{32}$, —$N(R^{33})COR^{34}$ and substituents represented by Formula B. $Z^2$ is selected from the group consisting of a direct bond, —$CR^{35}R^{36}$—, —O—, —$NR^{37}$—, —$NCOR^{38}$—, —S—, —SO—, and —$SO_2$—. Each of the R groups of $R^{20}$ to $R^{38}$ are independently selected from the group consisting of hydrogen, C3-C6 polyhydroxylated alkyl, —$((CH_2)_2$—O—$(CH_2)_2$—O$)_b$—$R^{40}$, C1-C10 alkyl, C5-C10 aryl, C5-C10 heteroaryl, —$(CH_2)_b$OH, —$(CH_2)_b CO_2H$, —$(CH_2)_b SO_3H$, —$(CH_2)_b SO_3^-$, —$(CH_2)_b OSO_3H$, —$(CH_2)_b OSO_3^-$, —$(CH_2)_b NHSO_3H$, —$(CH_2)_b NHSO_3^-$, —$(CH_2)_b PO_3H_2$, —$(CH_2)_b PO_3^-$, —$(CH_2)_b PO_3^-$, —$(CH_2)_b OPO_3H_2$, —$(CH_2)_b OPO_3H^-$ and —$(CH_2)_b OPO_3$. $R^{40}$ is selected from the group consisting of hydrogen, C1-C10 alkyl, C5-C10 aryl, C5-C10 heteroaryl, —$(CH_2)_b$OH, —$(CH_2)_b CO_2H$, —$(CH_2)_b SO_3H$, —$(CH_2)_b SO_3^-$, —$(CH_2)_b OSO_3H$, —$(CH_2)_b OSO_3^-$, —$(CH_2)_b NHSO_3H$, —$(CH_2)_b NHSO_3^-$, —$(CH_2)_b PO_3H_2$, —$(CH_2)_b PO_3H^-$, —$(CH_2)_b PO_3^-$, —$(CH_2)_b OPO_3H_2$, —$(CH_2)_b OPO_3H^-$ and —$(CH_2)_b OPO_3$. "p" and "q" independently fall within the range of 1 to 6 inclusive in some embodiments, and independently fall within the range of 1 to 3 inclusive in some embodiments. "b" is an integer from 1 to 10 inclusive in some embodiments, and is an integer from 1 to 6 inclusive in some embodiments.

In some embodiments represented by Formula II, $X^3$ and $X^4$ are independently —CN, —$CO_2R^{20}$ or —$CONR^{21}R^{22}$; $Y^3$ and $Y^4$ are independently —$NR^{31}R^{32}$ or a substituent of Formula B. In such embodiments, each of $R^{20}$, $R^{21}$, $R^{31}$ and $R^{32}$ is independently not hydrogen, C3-C6 polyhydroxylated alkyl, —$(CH_2)_2O$—$(CH_2)_2$—O$)_b$—$R^{40}$, C1-C10 alkyl or C1-C10 aryl. Further, p, q, N and $Z^2$ together do not form a 5- or 6-membered ring in such embodiments.

Formula II

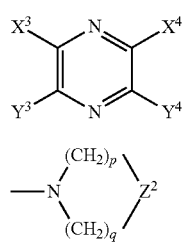

Formula B

—N$\begin{matrix}(CH_2)_p\\(CH_2)_q\end{matrix}$Z$^2$

In some embodiments represented by Formula II, $X^3$ and $X^4$ are independently selected from the group consisting of —CN, —$CO_2R^{20}$, —$CONR^{21}R^{22}$, —$SO_2R^{25}$ and —$SO_2OR^{26}$. $Y^3$ and $Y^4$ are independently selected from the group consisting of —$NR^{31}R^{32}$, —$N(R^{33})COR^{34}$ and substituents represented by Formula B. $Z^2$ is selected from the group consisting of a direct bond, —$CR^{35}R^{36}$—, —O—, —$NR^{37}$—, —$NCOR^{38}$—, —S—, —SO— and —$SO_2$—. Each of the R groups of $R^{20}$ to $R^{38}$ are independently selected from the group consisting of hydrogen, C3-C6 polyhydroxylated alkyl, —$((CH_2)_2$—O—$(CH_2)_2$—O$)_b$—$R^{40}$, C1-C10 alkyl, C5-C10 aryl, C5-C10 heteroaryl —$(CH_2)_b$OH, —$(CH_2)_b CO_2H$, —$(CH_2)_b SO_3H$ and —$(CH_2)_b SO_3^-$. In these embodiments, "b", "p" and "q" independently range from 1 to 3 inclusive.

Some embodiments represented by Formula II have $X^3$ and $X^4$ being independently selected from the group consisting of —CN, —$CO_2R^{20}$ and —$CONR^{21}R^{22}$. Each of $Y^3$ and $Y^4$ may be —$NR^{33}R^{34}$ or a substituent represented by Formula B. $Z^2$ is selected from the group consisting of a direct bond, —$CR^{16}R^{17}$, —O, —$NR^{18}$, —$NCOR^{19}$, —S, —SO and —$SO_2$. $R^{20}$ to $R^{38}$ are independently selected from the group consisting of hydrogen, C3-C6 polyhydroxylated alkyl, —$((CH_2)_2$—O—$(CH_2)_2$—O$)_b$—$R^{40}$, C1-C10 alkyl, —$(CH_2)_b$OH and —$(CH_2)_a CO_2H$. "b", "p" and "q" independently range from 1 to 3 inclusive.

By way of example, and not by way of limitation, compounds of Formula I and Formula II include the following (other exemplary compounds include those described in Examples 1-16):

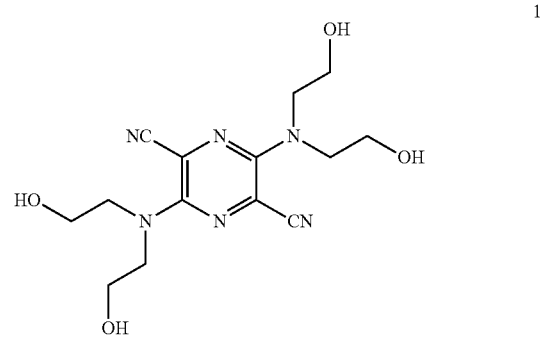

1

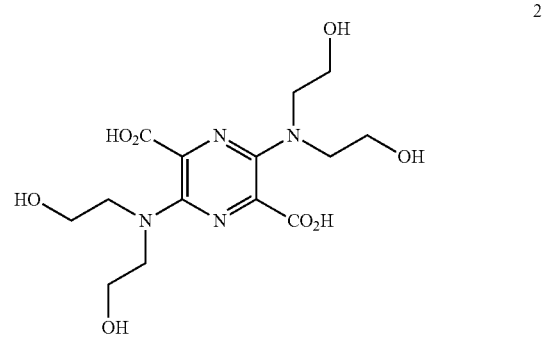

2

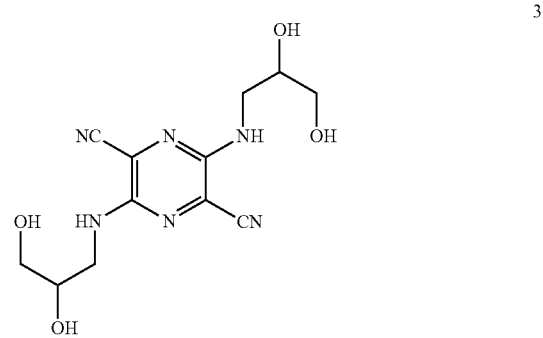

3

-continued

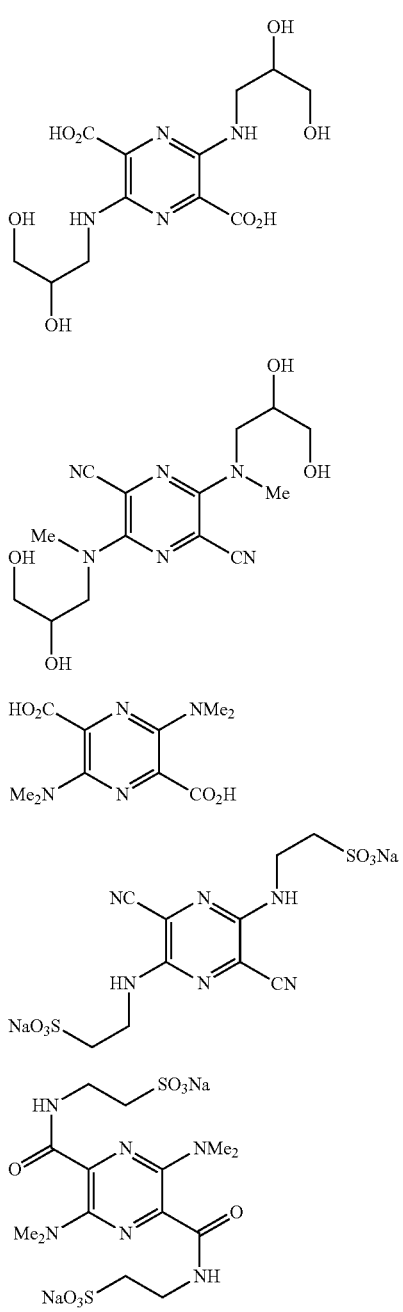

Syntheses of pyrazine derivatives, in general, has been previously studied [27] and described [25, 26, 28, 29]. Preparation procedures for at least some of the pyrazine derivatives disclosed herein, using procedures similar to the cited references, are described herein in Examples 1-8 and 12. Based on the cited references and the disclosure herein, one of ordinary skill in the art will be readily able to prepare compounds of the invention.

In accordance with one aspect of the present invention, compounds corresponding to Formula I may be derived from 2,5-diaminopyrazine-3,6-dicarboxylic acid which, in turn, may be derived from 5-aminouracil. For example, 5-aminouracil may be treated with a ferricyanide in the presence of a base to form, as an intermediate, 2,4,6,8-tetrahydroxypyrimido(4,5-g)pteridine (or a salt thereof), the pteridine intermediate is heated and hydrolyzed using a base, and the hydrolysate is then acidified to yield 2,5-diaminopyrazine-3,6-dicarboxylic as illustrated in Reaction Scheme 1.

Reaction Scheme 1

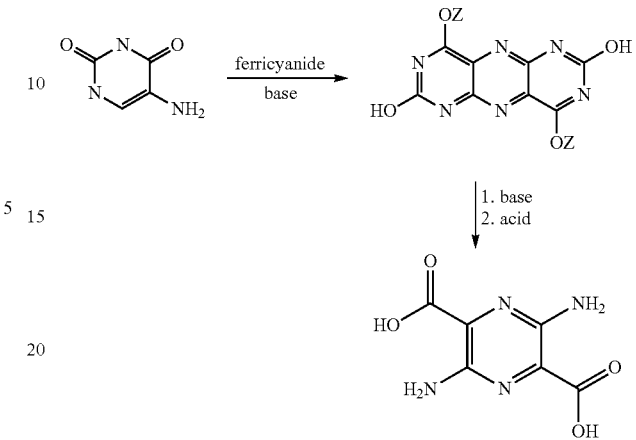

wherein each Z is independently hydrogen or a monovalent cation. For example, each Z may independently be hydrogen or an alkali metal. In one exemplary embodiment, each Z is hydrogen. In another exemplary embodiment, each Z is an alkali metal. In yet another exemplary embodiment, each Z is lithium, sodium or potassium, but they are different (e.g., one is potassium and the other is lithium or sodium).

The series of reactions illustrated in Reaction Scheme 1 are generally carried out in a suitable solvent. Typically, the reactions will be carried out in an aqueous system.

In one embodiment, each equivalent of 5-aminouracil is treated with about 3.0 equivalents of ferricyanide, and the concentration of the base is about 0.5N in the reaction mixture. The ferricyanide used to treat 5-aminouracil may be selected from the group consisting of potassium ferricyanide ($K_3Fe(CN)_6$), lithium ferricyanide ($Li_3Fe(CN)_6$), sodium ferricyanide ($Na_3Fe(CN)_6$), sodium potassium ferricyanide, lithium sodium ferricyanide or lithium potassium ferricyanide. Typically, the ferricyanide will be potassium ferricyanide. The base used in combination with the ferricyanide is preferably an alkali metal hydroxide, e.g., sodium or potassium hydroxide. See, for example, Taylor et al., JACS, 77: 2243-2248 (1955).

In a preferred embodiment, the hydrolysis mixture is irradiated with microwaves to heat the mixture as the 2,4,6,8-tetrahydroxypyrimido(4,5-g)pteridine (or salt thereof) is hydrolyzed. At least in some embodiments, the microwaves will have a frequency within the range of about 300 MHz to 30 GHz, and the hydrolysis mixture (preferably an aqueous hydrolysis mixture) is heated to a temperature within the range of about 120 to about 180° C. for a period of about 30 to about 90 minutes. For example, in some embodiments, the hydrolysis mixture will be irradiated with microwaves to heat the hydrolysis mixture to a temperature of about 120 to about 140° C. for about 45 to about 75 minutes. In addition to the 2,4,6,8-tetrahydroxypyrimido(4,5-g)pteridine (or salt thereof), the hydrolysis mixture of at least some embodiments will typically contain at least about 4.7 equivalents of a base, preferably an alkali metal hydroxide (e.g., potassium or sodium hydroxide). The resulting hydrolysate may then be acidified, preferably with a mineral acid such as hydrochloric acid, sulfuric acid, or phosphoric acid, more preferably hydrochloric acid, to provide 2,5-diaminopyrazine-3,6-dicarboxylate.

Methods for the conversion of 2,5-diaminopyrazine-3,6-dicarboxylic acid to other compositions falling within Formula I are known to those of ordinary skill. For example, corresponding 2,5-diaminopyrazine-3,6-diesters and corresponding 2,5-Bis(N,N-dialkylamino) pyrazine-3,6-diesters may be prepared by treating 2,5-diaminopyrazine-3,6-dicarboxylic acid with the appropriate alkylating agent(s), for example, a mono- or dialkyl halide as described in Kim et al., *Dyes and Pigments*, Vol. 39, pages 341-357 (1998). Alternatively, corresponding 2,5-diaminopyrazine-3,6-dithioesters or corresponding 2,5-Bis(N,N-dialkylamino) pyrazine-3,6-dithioesters may be prepared by treating the 2,5-diaminopyrazine-3,6-dicarboxylic acid with a thiol, or a thiol and the appropriate alkylating agent, respectively, as described in Kim et al., *Dyes and Pigments*, Vol. 41, pages 183-191 (1999).

It is noteworthy that the alkylation of the electron donating amino groups in cyano- or carboxypyrazines has a profound effect on electronic transition of the pyrazine chromophore in that the dialkylation of the amino group in 2,5-diamino-3,5-dicyanopyrazine produces large bathochromic shift on the order of about 40-60 nm. It is also noteworthy that the pyrrolidino and piperidino derivatives exhibit substantial differences in their UV spectra (e.g., the former may tend to exhibit a bathochromic shift of about 34 nm).

One protocol for assessing physiological function of renal cells includes administering an effective amount of a pyrazine derivative that is capable of being renally cleared into a body of a patient. This pyrazine derivative is hydrophilic and capable of absorbing and/or emanating spectral energy of at least about 400 nm. Examples of such pyrazine derivates are those represented by Formulas I and II above. An appropriate dosage of the pyrazine derivative that is administered to the patient is readily determinable by one of ordinary skill in the art and may vary according to such factors as clinical procedure contemplated, solubility, bioavailability, and toxicity. By way of example, an appropriate dosage generally ranges from about 1 nanomolar to about 100 micromolar. The administration of the pyrazine derivative to the patient may occur in any of a number of appropriate fashions including, but not limited to: (1) intravenous, intraperitoneal, or subcutaneous injection or infusion; (2) oral administration; (3) transdermal absorption through the skin; and (4) inhalation.

Still referring to the above-mentioned protocol, the pyrazine derivative in the patient's body is exposed to spectral energy of at least about 400 nm (preferably, visible and/or near infrared light). This exposure of the pyrazine derivative to spectral energy preferably occurs while the pyrazine derivative is in the body (e.g., in the bloodstream). Due to this exposure of the pyrazine derivative to the spectral energy, the pyrazine derivative emanates spectral energy (e.g., visible and/or near infrared light) that may be detected by appropriate detection equipment. The spectral energy emanated from the pyrazine derivative tends to exhibit a wavelength range greater than a wavelength range absorbed by the pyrazine derivative. For example, if a composition of the invention absorbs light of about 700 nm, the composition may emit light of about 745 nm.

Detection of the pyrazine derivative (or more particularly, the light emanating therefrom) may be achieved through optical fluorescence, absorbance, light scattering or other related procedures known in the art. In some embodiments, this detection of the emanated spectral energy may be characterized as a collection of the emanated spectral energy and a generation of electrical signal indicative of the collected spectral energy. The mechanism(s) utilized to detect the spectral energy from the composition that is present in the body may be designed to detect only selected wavelengths (or wavelength ranges) and/or may include one or more appropriate spectral filters. Various catheters, endoscopes, ear clips, hand bands, head bands, forehead sensors, surface coils, finger probes and the like may be utilized to expose the pyrazine derivatives to light and/or to detect the light emanating therefrom [30]. This detection of spectral energy may be accomplished at one or more times intermittently or may be substantially continuous.

Renal function of the patient can be determined based on the detected spectral energy. This can be achieved by using data indicative of the detected spectral energy and generating an intensity/time profile indicative of a clearance of the pyrazine derivative from the body. This profile may be correlated to a physiological or pathological condition. For example, the patient's clearance profiles and/or clearance rates may be compared to known clearance profiles and/or rates to assess the patient's renal function and to diagnose the patient's physiological condition. In the case of analyzing the presence of the pyrazine derivative in bodily fluids, concentration/time curves may be generated and analyzed (preferably in real time) using an appropriate microprocessor to diagnose renal function.

Physiological function can be assessed by any of a number of procedures such as any of the following or similar procedures alone or in any combination: (1) comparing differences in manners in which normal and impaired cells remove a composition of the invention from the bloodstream; (2) measuring a rate or an accumulation of a composition of the invention in the organs or tissues; and (3) obtaining tomographic images of organs or tissues having a composition of the invention associated therewith. For example, blood pool clearance may be measured non-invasively from convenient surface capillaries such as those found in an ear lobe or a finger or can be measured invasively using an appropriate instrument such as an endovascular catheter. Accumulation of a composition of the invention within cells of interest can be assessed in a similar fashion. Incidentally, a "composition" of the invention refers to sterile formulations, aqueous formulations, parenteral formulations and any other formulations including one or more of the pyrazine derivatives of the invention. These compositions of the invention may include pharmaceutically acceptable diluents, carriers, adjuvants, preservatives, excipients, buffers, and the like. The phrase "pharmaceutically acceptable" means those formulations which are, within the scope of sound medical judgment, suitable for use in contact with the tissues of humans and animals without undue toxicity, irritation, allergic response and the like, and are commensurate with a reasonable benefit/risk ratio.

A modified pulmonary artery catheter may also be utilized to, inter alia, make the desired measurements [32] of spectral energy emanating from a composition of the invention. The ability for a pulmonary catheter to detect spectral energy emanating from a composition of the invention is a distinct improvement over current pulmonary artery catheters that measure only intravascular pressures, cardiac output and other derived measures of blood flow. Traditionally, critically ill patients have been managed using only the above-listed parameters, and their treatment has tended to be dependent upon intermittent blood sampling and testing for assessment of renal function. These traditional parameters provide for discontinuous data and are frequently misleading in many patient populations.

Modification of a standard pulmonary artery catheter only requires making a fiber optic sensor thereof wavelength-specific. Catheters that incorporate fiber optic technology for measuring mixed venous oxygen saturation exist currently. In one characterization, it may be said that the modified pulmonary artery catheter incorporates a wavelength-specific optical sensor into a tip of a standard pulmonary artery catheter. This wavelength-specific optical sensor can be utilized to monitor renal function-specific elimination of a designed optically detectable chemical entity such as the compositions of the present invention. Thus, by a method analogous to a dye dilution curve, real-time renal function can be monitored by the disappearance/clearance of an optically detected compound.

The following examples illustrate specific embodiments of this invention. As would be apparent to skilled artisans, various changes and modifications are possible and are contemplated within the scope of the invention described.

Example 1

Prophetic

Preparation of 3,6-dicyano-2,5-[(N,N,N',N'-tetrakis(carboxymethyl)amino]pyrazine

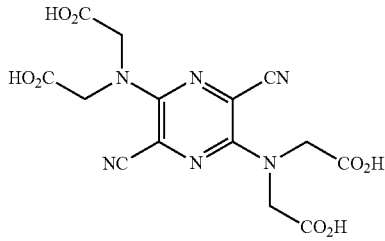

Step 1. A stirring mixture of 2,5-diamino-3,6-dicyanopyrazine (10 mmol) and t-butyl bromoacetate (42 mmol) in distilled dimethylacetamide (25 mL) is cooled in ice and subsequently treated with powdered sodium hydroxide (50 mmol). After stirring at ambient temperature for about 2 hours, the reaction mixture is treated water (200 mL) and methylene chloride (100 mL). An organic layer of the mixture is washed with copious water, next dried over sodium sulfate, then filtered, and subsequently the filtrate evaporated in vacuo. The crude product is then purified by flash chromatography to give tetra-t-butyl ester.

Step 2. The tetraester from Step 1 (10 mmol) is treated with 96% formic acid (10 mL) and heated to boiling for about 1 minute and kept at about 40-50° C. for approximately 16 hours. The reaction mixture is poured onto ether causing formation of a precipitate. This resulting precipitate is separated from the ether layer by decantation, and then purified by chromatography or recrystallization.

Example 2

Prophetic

Preparation of 3,6-[(N,N,N',N'-tetrakis(2-hydroxyethyl)amino]pyrazine-2,5-dicarboxylic acid

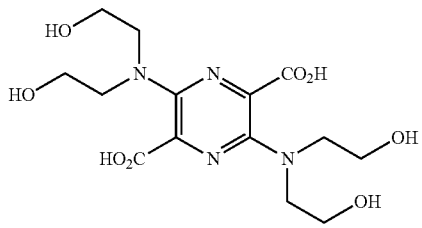 [SMILES: O=C(O)c1nc(N(CCO)CCO)c(C(=O)O)nc1N(CCO)CCO]

Step 1. The alkylation procedure is identical to the one in Step 1 of Example 1, except that 2-iodoethanol is used instead of t-butylbromoacetate.

Step 2. The dicyano compound from Step 1 (10 mmol) is dissolved in concentrated sulfuric acid (10 mL) and stirred at ambient temperature for about 3 hours. The reaction mixture is carefully diluted with water (100 mL), and the product is collected by filtration and subsequently dried to give the corresponding carboxamide intermediate.

Step 3. The biscarboxamide derivative from Step 2 (10 mmol) is dissolved in potassium hydroxide solution (25 mmol in 25 mL of water) and heated under reflux for about 3 hours. After cooling, the solution is acidified with 1N HCl (25 mL). The product is collected by filtration, dried, and purified by recrystallization or chromatography.

Preparation of 3,5-[(N,N,N',N'-tetrakis(2-hydroxyethyl)amino]pyrazine-2,6-dicarboxylic acid (compound of Formula II) can be accomplished in a similar manner using 2,6-diamino-3,5-dicyanopyazine as the starting material.

Alternatively, 3,6-[(N,N,N',N'-tetrakis(2-hydroxyethyl)amino]pyrazine-2,5-dicarboxylic acid may be prepared by N-alkylating 3,6-diaminopyrazine-2,5-dicarboxylic acid (Example 16) with 2-iodoethanol as described in Step 1.

Example 3

Prophetic

Preparation of 3,6-bis(N-azetadino)pyrazine-2,5-dicarboxylic acid

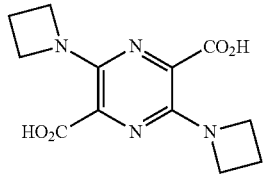 [SMILES: O=C(O)c1nc(N2CCC2)c(C(=O)O)nc1N1CCC1]

Step 1. The alkylation procedure is substantially identical to the one in Step 1 of Example 1, except that 1,3-dibromopropane is used instead of t-butylbromoacetate.

Step 2. The hydrolysis procedure is substantially identical to the one in Step 2 of Example 2, except that the starting material is 3,6-dicyano-2,5-bis(N-azetadino)pyrazine.

Step 3. The hydrolysis procedure is substantially identical to the one in Step 3 of Example 2, except that the starting material is 3,6-bis(N-azetadino)-2,5-pyrazinedicarboxamide.

Preparation of 3,5-bis(N-azetadino)pyrazine-2,6-dicarboxylic acid (compound of Formula II) can be accomplished in a similar fashion using 2,6-diamino-3,5-dicyanopyazine as the starting material.

Alternatively, 3,6-bis(N-azetadino)pyrazine-2,5-dicarboxylic acid may be prepared by N-alkylating 3,6-diaminopyrazine-2,5-dicarboxylic acid (Example 16) with 1,3-dibromopropane as described in Step 1.

Example 4

Prophetic

Preparation of 3,6-bis(N-morpholino)pyrazine-2,5-dicarboxylic acid

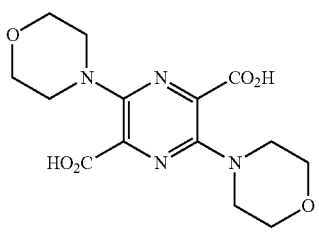 [SMILES: O=C(O)c1nc(N2CCOCC2)c(C(=O)O)nc1N1CCOCC1]

Step 1. The alkylation procedure is identical to the one in Step 1, Example 1 except that bis(2-chloroethyl)ether is used instead of t-butylbromoacetate.

Step 2. The hydrolysis procedure is identical to the one in Step 2, Example 2 except that the starting material is 3,6-dicyano-2,5-bis(N-morpholino)pyrazine.

Step 3. The hydrolysis procedure is identical to the one in Step 3, Example 2 except that the starting material is 3,6-bis(N-morpholino)-2,5-pyrazinedicarboxamide.

Preparation of 3,5-bis(N-morpholino)pyrazine-2,6-dicarboxylic acid (compound belonging to Formula II) can be accomplished in the same manner using 2,6-diamino-3,5-dicyanopyazine as the starting material.

Alternatively, 3,6-bis(N-morpholino)pyrazine-2,5-dicarboxylic acid may be prepared by N-alkylating 3,6-diaminopyrazine-2,5-dicarboxylic acid (Example 16) with (2-chloroethyl)ether as described in Step 1.

Example 5

Prophetic

Preparation of 3,6-bis(N-piperazino)pyrazine-2,5-dicarboxylic acid

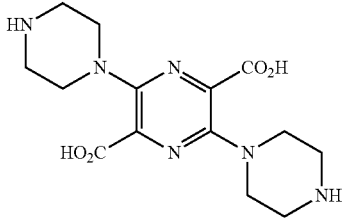 [SMILES: O=C(O)c1nc(N2CCNCC2)c(C(=O)O)nc1N1CCNCC1]

Step 1. The alkylation procedure is identical to the one in Step 1, Example 1 except that bis(2-chloroethyl) amine is used instead of t-butylbromoacetate.

Step 2. The hydrolysis procedure is identical to the one in Step 2, Example 2 except that the starting material is 3,6-dicyano-2,5-bis(N-piperazino)pyrazine.

Step 3. The hydrolysis procedure is identical to the one in Step 3, Example 2 except that the starting material is 3,6-bis(N-piperazino)-2,5-pyrazinedicarboxamide.

Preparation of 3,5-bis(N-piperazino)pyrazine-2,6-dicarboxylic acid (compound belonging to Formula II) can be accomplished in the same manner using 2,6-diamino-3,5-dicyanopyazine as the starting material.

Alternatively, 3,6-bis(N-piperazino)pyrazine-2,5-dicarboxylic acid may be prepared by N-alkylating 3,6-diaminopyrazine-2,5-dicarboxylic acid (Example 16) with bis(2-chloroethyl) amine as described in Step 1.

Example 6

Prophetic

Preparation of 3,6-bis(N-thiomorpholino)pyrazine-2,5-dicarboxylic acid

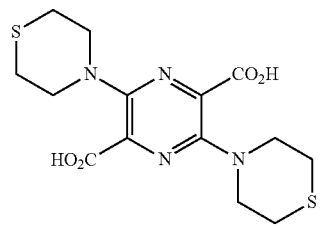 [SMILES: O=C(O)c1nc(N2CCSCC2)c(C(=O)O)nc1N1CCSCC1]

Step 1. A mixture of the tetralcohol product from Step 1, Example 2, (10 mmol), and triethylamine (44 mmol) in anhydrous tetrahydrofuran (50 mL) cooled to 0° C. and treated with methanesulfonyl chloride (42 mmol) added in portion in such a manner that the temperature is maintained at 0 to 15° C. After the addition, the reaction mixture is stirred at ambient temperature for 16 hours. The reaction mixture is then filtered and the filtrate taken to dryness under reduced pressure. The residue is then redissolved in methanol (20 mL) and treated with sodium sulfide (22 mmol). The reaction mixture is then heated under reflux for 16 hours and poured onto water (100 mL) and extracted with ethyl acetate. The combined organic layer is washed with copious water, dried over sodium sulfate, filtered, and the filtrate evaporated in vacuo. The crude product is then purified by flash chromatography to give the bis(thiomorpholino)pyrazine diester.

Step 2. The hydrolysis procedure is identical to the one in Step 2, Example 2 except that the starting material is 3,6-dicyano-2,5-bis(N-thiomorpholino)pyrazine.

Step 3. The hydrolysis procedure is identical to the one in Step 3, Example 2 except that the starting material is 3,6-bis(N-thiomorpholino)-2,5-pyrazinedicarboxamide.

Preparation of 3,5-bis(N-thiomorpholino)pyrazine-2,6-dicarboxylic acid (compound belonging to Formula II) can be accomplished in the same manner using 2,6-diamino-3,5-dicyanopyazine as the starling material.

Example 7

Prophetic

Preparation of
3,6-bis(N-thiomorpholino)pyrazine-2,5-dicarboxylic
acid S-oxide

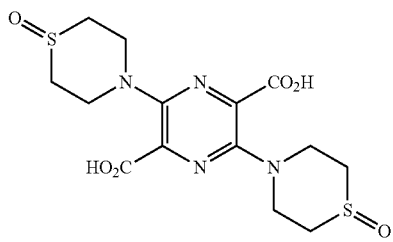 [SMILES: O=C(O)c1nc(N2CCS(=O)CC2)c(C(=O)O)nc1N1CCS(=O)CC1]

Step 1. The bis(thiomorpholino)pyrazine derivative from Step 3, Example 6 (5 mmol) is dissolved in methanol (20 mL) and treated with m-chloroperoxybenzoic acid (11 mmol) and heated under reflux for 16 hours. The reaction mixture poured onto saturated sodium bicarbonate (20 mL) and extracted with methylene chloride. The combined organic layer is washed with brine, dried over sodium sulfate, filtered, and the filtrate evaporated in vacuo. The crude product is purified by chromatography or recrystallization.

Step 2. The procedure is identical to Step 2, Example 6 except that thiomorpholino-5-oxide is used in this experiment.

Preparation of 3,5-bis(N-thiomorpholino)pyrazine-2,6-dicarboxylic acid S-oxide (compound belonging to Formula II) can be accomplished in the same manner using 2,6-diamino-3,5-dicyanopyazine as the starting material, followed by hydrolysis of the nitrile as outlined in Example 1, Step 2 or Example 2, Steps 2 and 3.

Example 8

Prophetic

Preparation of
2,5-dicyano-3,6-bis(N-thiomorpholino)pyrazine
S,S-dioxide

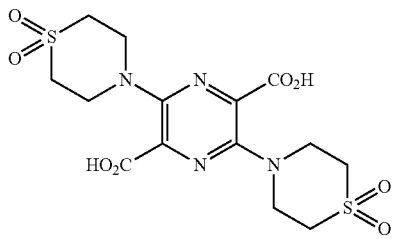 [SMILES: O=C(O)c1nc(N2CCS(=O)(=O)CC2)c(C(=O)O)nc1N1CCS(=O)(=O)CC1]

Step 1. The procedure is identical to Step 1, Example 7 except that thiomorpholino-5-oxide is used in this experiment.

Step 2. The procedure is identical to Step 2, Example 6 except that thiomorpholino-S,S-dioxide is used in this experiment.

Example 9

Prophetic

Protocol for Assessing Renal Function.

Figure 4:
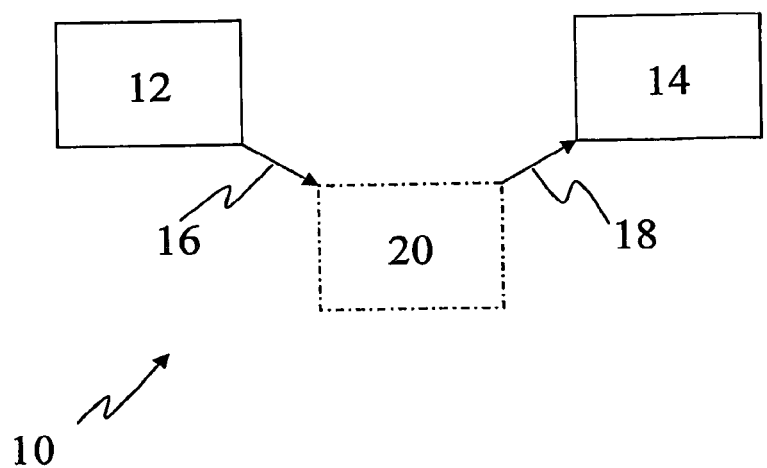
FIG. 4: Block diagram of an assembly for assessing renal function.

An example of an in vivo renal monitoring assembly 10 is shown in FIG. 4 and includes a light source 12 and a data processing system 14. The light source 12 generally includes or is interconnected with an appropriate device for exposing at least a portion of a patient's body to light therefrom. Examples of appropriate devices that may be interconnected with or be a part of the light source 12 include, but are not limited to, catheters, endoscopes, fiber optics, ear clips, hand bands, head bands, forehead sensors, surface coils, and finger probes. Indeed, any of a number of devices capable of emitting visible and/or near infrared light of the light source may be employed in the renal monitoring assembly 10.

Still referring to FIG. 4, the data processing system 14 of the renal monitoring assembly 10 may be any appropriate system capable of detecting spectral energy and processing data indicative of the spectral energy. For instance, the data processing system 14 may include one or more lenses (e.g., to direct and/or focus spectral energy), one or more filters (e.g., to filter out undesired wavelengths of spectral energy), a photodiode (e.g., to collect the spectral energy and convert the same into electrical signal indicative of the detected spectral energy), an amplifier (e.g., to amplify electrical signal from the photodiode), and a processing unit (e.g., to process the electrical signal from the photodiode). This data processing system 14 is preferably configured to manipulate collected spectral data and generate an intensity/time profile and/or a concentration/time curve indicative of renal clearance of a pyrazine composition of the present invention from the patient 20. Indeed, the data processing system 14 may be configured to generate appropriate renal function data by comparing differences in manners in which normal and impaired cells remove the pyrazine composition from the bloodstream, to determine a rate or an accumulation of the composition in organs or tissues of the patient 20, and/or to provide tomographic images of organs or tissues having the pyrazine composition associated therewith.

In one protocol for determining renal function, an effective amount of a composition including a pyrazine derivative of the invention is administered to the patient. At least a portion of the body of the patient 20 is exposed to visible and/or near infrared light from the light source 12 as indicated by arrow 16. For instance, the light from the light source 12 may be delivered via a fiber optic that is affixed to an ear of the patient 20. The patient may be exposed to the light from the light source 12 before or after administration of the composition to the patient 20. In some cases, it may be beneficial to generate a background or baseline reading of light being emitted from the body of the patient 20 (due to exposure to the light from the light source 12) before administering the composition to the patient 20. When the pyrazine derivative(s) of the composition that are in the body of the patient 20 are exposed to the light from the light source 12, the pyrazine derivative(s) emanate light (indicated by arrow 18) that is detected/collected by the data processing system 14. Initially, administration of the composition to the patient 20 generally enables an initial spectral signal indicative of the initial content of the pyrazine derivative(s) in the patient 20. The spectral signal then tends to decay as a function of time as the pyrazine derivative(s) is cleared from the patient 20. This decay in the spectral signal as a function of time is indicative of the patient's renal function. For example, in a first patient exhibiting healthy/normal renal function, the spectral signal may decay back to a baseline in a time of T. However, a spectral signal indicative of a second patient exhibiting deficient renal function may decay back to a baseline in a time of T+4 hours. As such, the patient 20 may be exposed to the light from the light source 12 for any amount of time appropriate for providing the desired renal function data. Likewise, the data processing system 14 may be allowed to collect/detect spectral energy for any amount of time appropriate for providing the desired renal function data.

Example 10

Actual

Assessment of Renal Function of Normal Rat.

Figure 5:
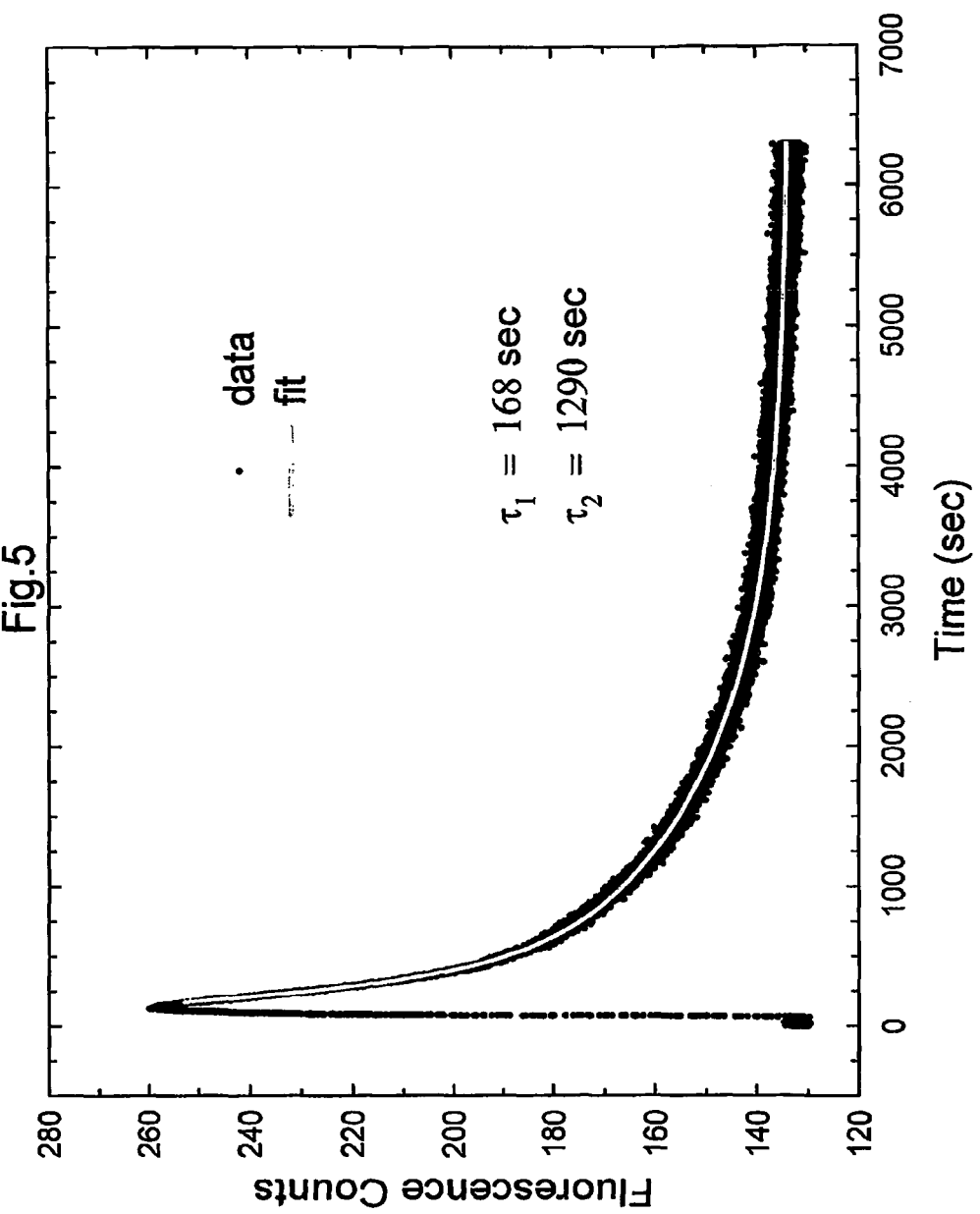
FIG. 5: Graph showing renal clearance profile of a normal rat.

Incident laser light having a wavelength of about 470 nm was delivered from a fiber optic bundle to the ear of an anesthetized Sprague-Dawley rat. While the light was being directed at the ear, data was being acquired using a photodetector to detect fluorescence coming from within the ear. A background reading of fluorescence was obtained prior to administration of the pyrazine agent. Next, the pyrazine agent (in this case, 2 ml of a 0.4 mg/ml solution of 3,6-diaminopyrazine-2,5-dicarboxylic acid in PBS) (Example 16) was administered into the rat through a bolus injection in the lateral tail vein. As shown in FIG. 5, shortly after the injection, the detected fluorescence signal rapidly increased to a peak value. The signal then decayed as a function of time indicating the dye being cleared from the bloodstream (in this case, over a duration of a little over 20 minutes).

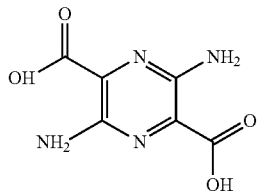 [SMILES: Nc1nc(C(=O)O)c(N)nc1C(=O)O]

3,6-diaminopyrazine-2,5-dicarboxylic acid

The blood clearance time profiles reported herein were assumed to follow a two compartment pharmacokinetic model. The fluorescent signal (arising from the dye concentration in the blood) as a function of time was therefore fit to a double exponential decay. The equation employed to fit the data was:

$$S = Ae^{-t/\tau_1} + Be^{-t/\tau_2} + C \quad (1)$$

where S is the fluorescent light intensity signal measured, t is the time point of the measurement, and e refers to the mathematical constant having a numerical value of about 2.71828182846. The decay times $\tau_1$ and $\tau_2$, and the constants A, B, and C are deduced from the fitting procedure. The non-linear regression analysis package within SigmaPlot® (Systat Software Inc., Richmond, Calif.) was employed to fit data to Eq. (1). In Examples 10 and 11, $\tau_1$ represents the time constant for vascular-extracellular fluid equilibrium, and $\tau_2$ represents the dye clearance from the blood.

Example 11

Actual

Assessment of Renal Function of Bilaterally Nephrectomized Rat.

Figure 6:
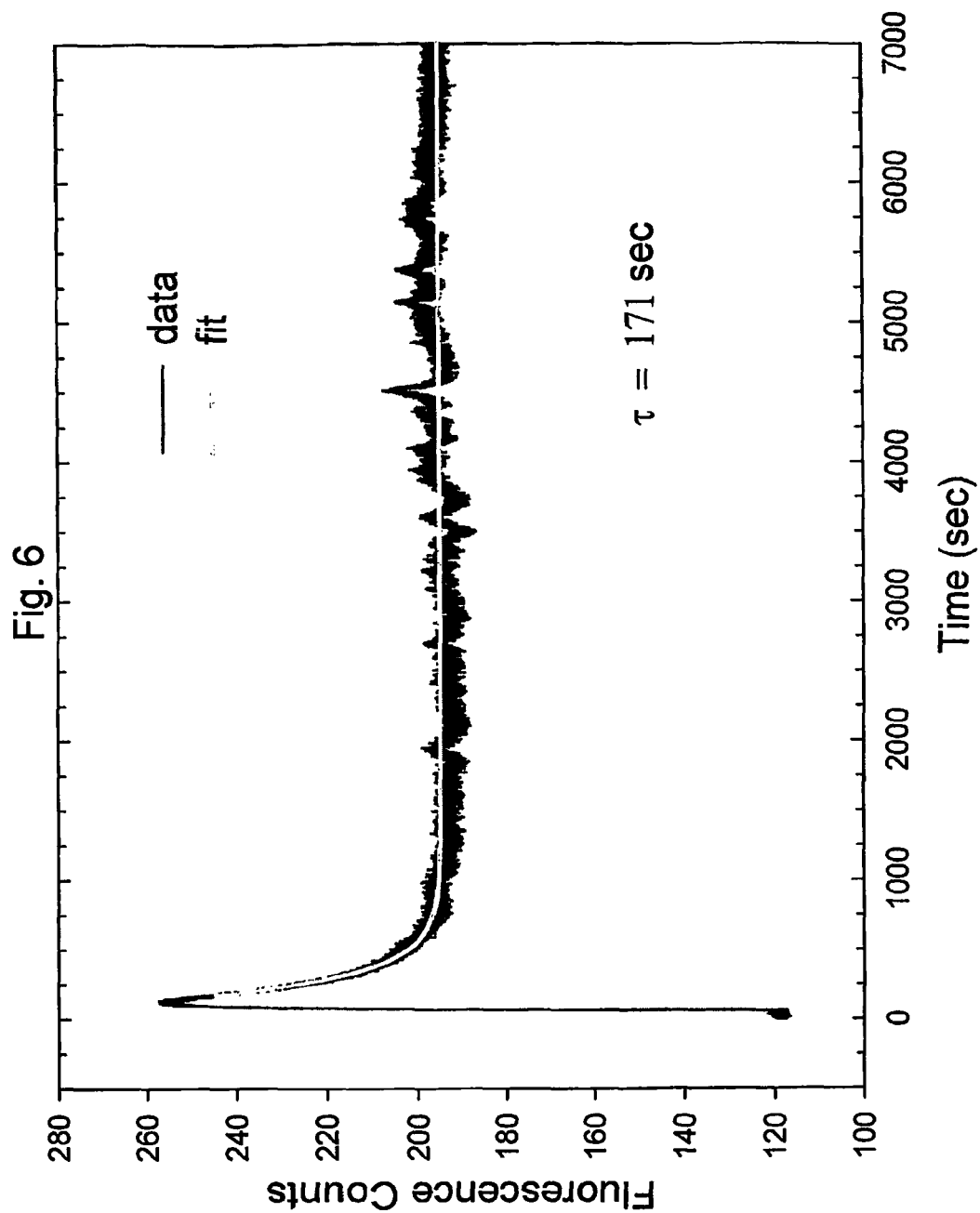
FIG. 6: Graph showing renal clearance profile of a bilaterally nephrectomized rat.
Figure 7:
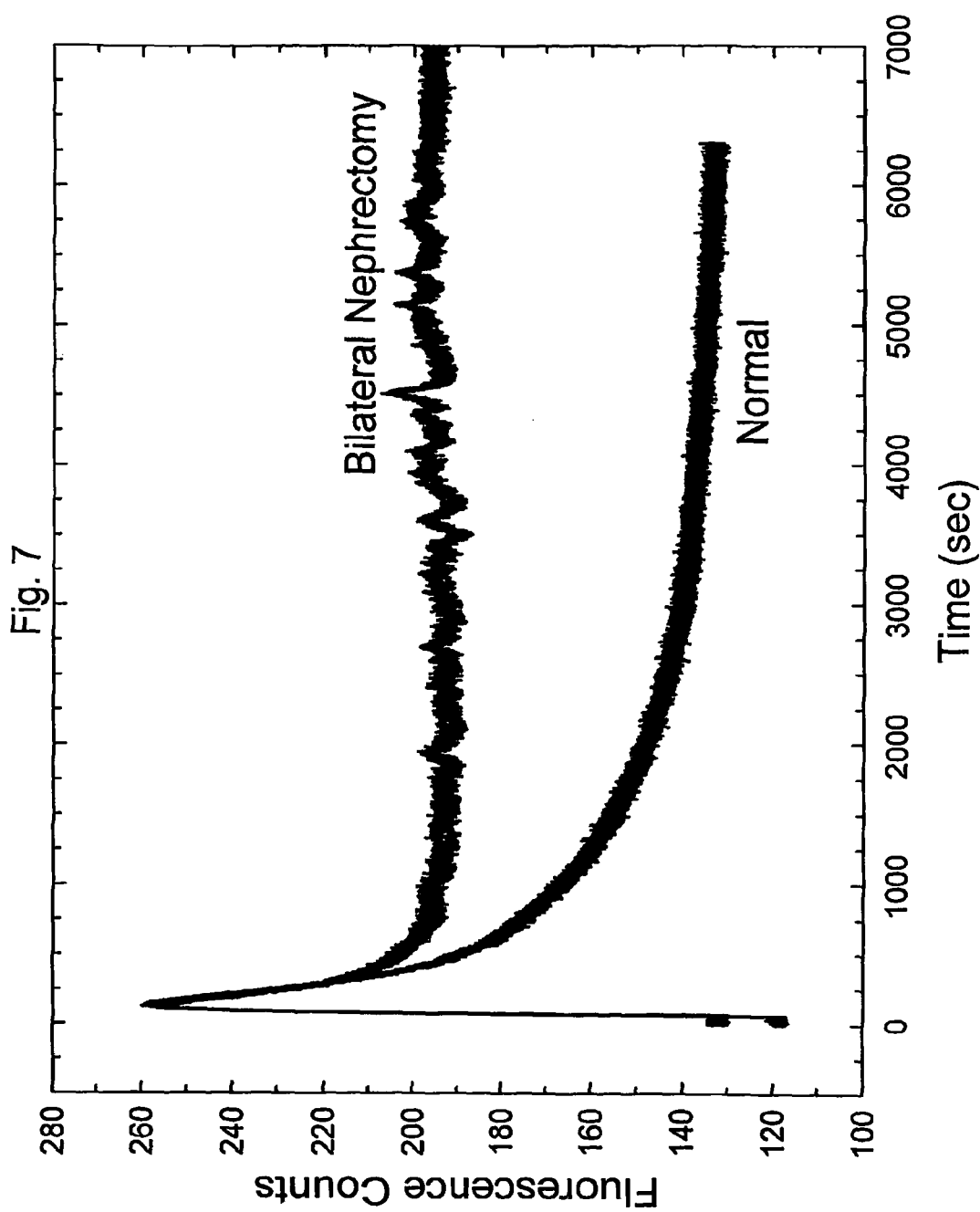
FIG. 7: Graph comparing data of FIGS. 5 and 6.

An anesthetized Sprague-Dawley rat was bilaterally nephrectomized. Incident laser light having a wavelength of about 470 nm was delivered from a fiber optic bundle to the ear of rat. While the light was being directed at the ear, data was being acquired using a photodector to detect fluorescence coming from within the ear. A background reading of fluorescence was obtained prior to administration of the pyrazine agent. Next, the pyrazine agent (again, in this case, 2 ml of a 0.4 mg/ml solution of 3,6-diaminopyrazine-2,5-dicarboxylic acid in PBS) was administered into the rat through a bolus injection in the lateral tail vein. As shown in FIG. 6, shortly after the injection, the detected fluorescence signal rapidly increased to a peak value. However, in this case, the pyrazine agent did not clear, indicating that the agent is capable of being renally cleared. A comparison between the rat that exhibited normal kidney function (FIG. 5) and the rat that had a bilateral nephrectomy (FIG. 6) is shown in FIG. 7. Incidentally, experiments similar to those of Examples 10 and 11 can be utilized to determine whether or not other proposed agents are capable of being renally cleared.

Example 12

Actual

Preparation of 3,6-dicyano-2,5-[(N,N,N',N'-tetrakis (carboxymethyl)amino]pyrazine

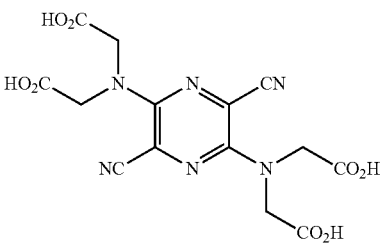 [SMILES: N#Cc1nc(N(CC(=O)O)CC(=O)O)c(C#N)nc1N(CC(=O)O)CC(=O)O]

Step 1. A stirring mixture of 2,5-diamino-3,6-dicyanopyrazine (1 mmol) and t-butyl bromoacetate (16 mmol) in dimethylacetamide (5 mL) was cooled in an ice-water-bath and subsequently treated with powdered NaOH (6 mmol). The contents were allowed to warm to ambient temperature over 1 h, then the reaction mixture was treated with deionized water (50 mL). This aqueous mixture was extracted twice with methylene chloride (50 mL). The combined organic extracts were dried over sodium sulfate, filtered, and concentrated in vacuo to afford an oil. This oil was purified by flash chromatography to give the tetra-t-butyl ester.

Step 2. The tetraester from Step 1 (0.86 mmol) was heated in glacial acetic acid (50 mL) for 24 hours, then was allowed to cool to ambient temperature. The solution was filtered and concentrated in vacuo to afford an oil. The oil was purified by preparative HPLC to afford the title compound.

Example 13

Prophetic

Preparation of 2,6-dicyano-3,5-[(N,N,N',N'-tetrakis(hydroxyethyl)amino]pyrazine

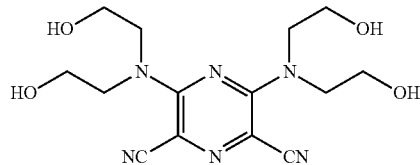 [SMILES: N#Cc1nc(C#N)c(N(CCO)CCO)nc1N(CCO)CCO]

To a stirring solution of mixture of tetracyanopyrazine (10 mmol) in tetrahydrofuran (25 mL) is treated with dropwise addition of diethanolamine (50 mmol) over 30 minutes. After the addition, the mixture is stirred at ambient temperature for additional 1 hour. The crude product is collected by filtration and purified by chromatography or recrystallization.

Example 14

Prophetic

Preparation of 2,6-dicyano-3,5-[(N,N'-bis(hydroxyethyl)amino]pyrazine

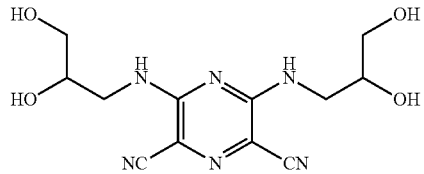 [SMILES: N#Cc1nc(C#N)c(NCC(O)CO)nc1NCC(O)CO]

The procedure is identical to Example 13 except that aminopropanediol is used in instead of diethanolamine.

Example 15

Prophetic

Preparation of 2,6-dicyano-3,5-[(N,N'-bis(prolyl)amino]pyrazine

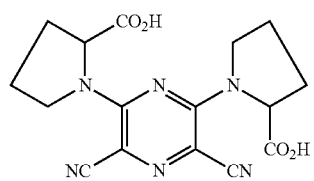 [SMILES: N#Cc1nc(C#N)c(N2CCCC2C(=O)O)nc1N1CCCC1C(=O)O]

The procedure is identical to Example 13 except that proline is used in instead of diethanolamine.

Example 16

Actual

Synthesis of 3,6-diaminopyrazine-2,5-dicarboxylic acid

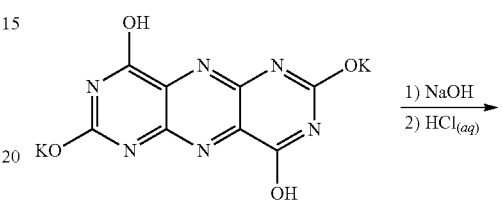

dipotassium 2,4,6,8-tetrahydroxy-pyrimido[4,5g]pteridine

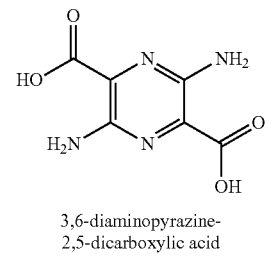

3,6-diaminopyrazine-2,5-dicarboxylic acid

Dipotassium 2,4,6,8-tetrahydroxypyrimido(4,5-g)pteridine was prepared by treating 5-aminouracil with potassium ferricyanide in the presence of potassium hydroxide as described in Taylor et al., *JACS*, 77: 2243-2248 (1955).

In each of two Teflon reaction vessels was placed 0.5 g dipotassium 2,4,6,8-tetrahydroxypyrimido[4,5g,]pteridine and a solution consisting of 0.3-0.4 g sodium hydroxide in about 10 mL deionized water. The vessels were secured in the microwave reactor and allowed to react for one hour at 170° C., generating ca. 100 psi pressure, for one hour. The vessels were allowed to cool in the microwave to ca. 50° C. and the contents filtered to remove a small amount of solid residue. The bright yellow filtrate was transferred to a 250 mL round-bottom flask equipped with a large magnetic stir bar. With stirring, the pH was adjusted to ca. 3 with concentrated HCl. A large amount of red precipitate formed. A few more drops of acid was added and the solid collected by filtration on a glass frit, washed with cold 1×10 mL 1N HCl, 2×30 mL acetonitrile and 1×30 mL diethyl ether, suctioned dry and transferred to a vacuum oven, vacuum drying overnight at 45-50° C. Yield 0.48 g (79%). C13 NMR ($D_2O$/NaOD, external TMS reference) δ 132.35, 147.32, 171.68.

Figure 8A:
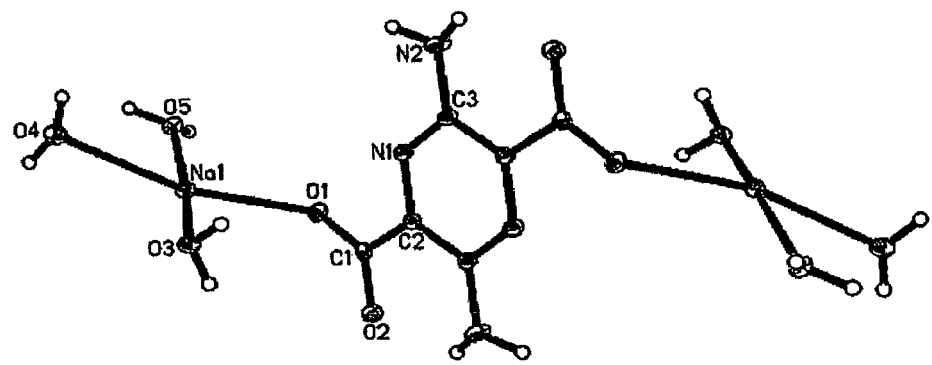
FIGS. 8A & 8B: Projection view of disodium 2,5-diamino-3,6-(dicarboxylato)pyrazine crystals prepared as set forth in Example 16.
Figure 8B:
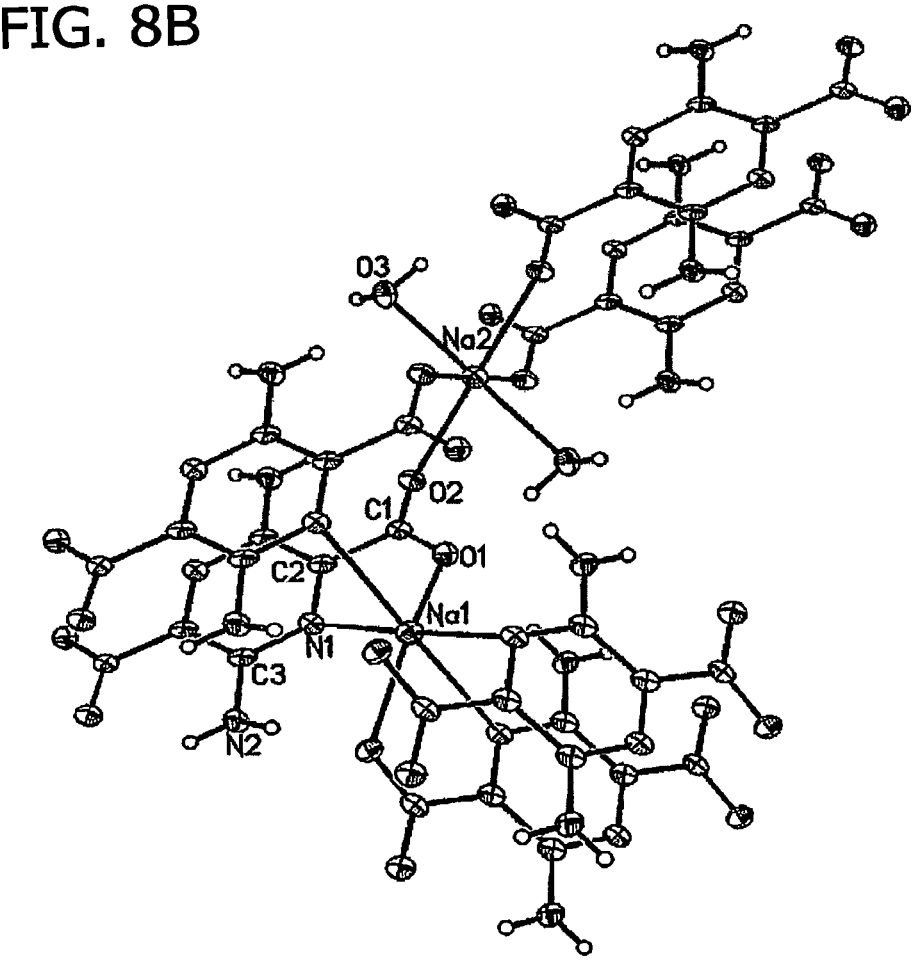

An aliquot of the bright yellow solution was concentrated in vacuo resulting in the formation of two sets of crystals: red needles and yellow blocks. X-Ray crystallography revealed that both crystals are disodium 2,5-diamino-3,6-(dicarboxylato)pyrazine. The crystal data and structure refinement for the two sets of crystals are set forth in Tables 1R-6R (red crystals) and Tables 1Y-6Y (yellow blocks). Their structures are shown in FIGS. 8A (projection view of the molecule with 50% thermal ellipsoids) and 8B (projection view of the molecule with 50% thermal ellipsoids and coordination sphere of the Na atoms).

Example 17

Prophetic

Preparation of 2,5-dicyano 3,6-[(N,N'-bis(2,3-dihydroxyhydroxypropyl)amino]-pyrazine

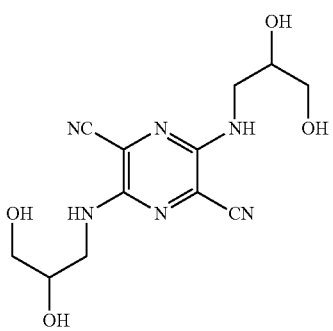

3

The alkylation procedure is identical to the one in Step 1 of Example 1, except that 3-bromo-1,2-propanediol is used instead of t-butylbromoacetate.

Example 18

Prophetic

Preparation of 3,6-[(N',N'-bis(2,3-dihydroxypropyl)amino]pyrazine-2,5-dicarboxylic acid

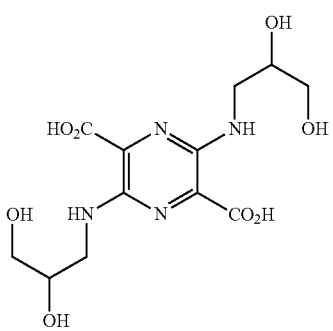

4

Step 1. The alkylation procedure is identical to the one in Step 1 of Example 1, except that 3-bromo-1,2-propanediol is used instead of t-butylbromoacetate.

Step 2. The hydrolysis procedure is identical to the one in Step 2 of Example 2, except that the starting material is the cyano compound in Example 17.

Step 3. The hydrolysis procedure is identical to the one in Step 3.

Example 19

Prophetic

Preparation of 2,5-dicyano 3,6-[(N,N'-bis(2,3-dihydroxyhydroxypropyl)amino]-N,N'-dimethylaminopyrazine

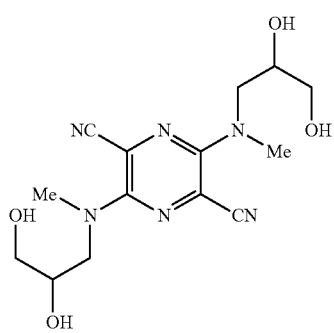

5

The cyano compound (10 mmol) from Example 17 is dissolved in dimethylformamide (10 mL) and treated with dimethylsulfate (30 mmol). The mixture is heated at 100° C. for 4 hours and triturated with acetone (100 mL). The crude product is then collected and purified by either crystallization or chromatography.

Example 20

Prophetic

Preparation of 3,6-[(N,N-bis(dimethylamino]pyrazine-2,5-dicarboxylic acid

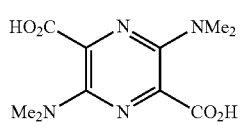

6

The title compound is prepared by the hydrolysis of the corresponding dicyano compound by the procedure described in Steps 2 and 3 of Example 2.

Example 21

Prophetic

Preparation of 2,5-dicyano 3,6-[(N,N'-bis(2,-sulfonatoethyl)amino]-pyrazine

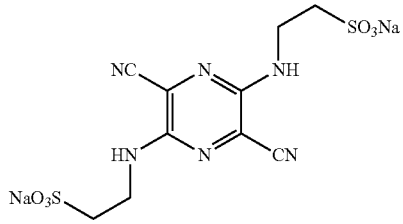

7

The alkylation procedure is identical to the one in Step 1 of Example 1, except that taurine (2-aminoethanesulfonate) is used instead of t-butylbromoacetate.

Example 22

Prophetic

Preparation of 2,5-bis[(N,N'-(2-sulfonato)ethyl]carbamoyl-3,6-[(N,N-bis-(dimethylamino)]pyrazine

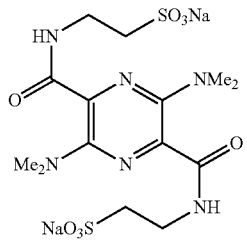

A mixture of the diacid in Example 20 (10 mmol), taurine (22 mmol) and the water-soluble carbodiimide, EDC (ethyldimethylaminopropylcarbodiimide) (25 mmol) in water/DMF (1:1) is stirred at ambient temperature for 16 hours. The solvent is evaporated in vacuo and the crude product is purified by chromatography.

TABLE 1Y

Crystal data and structure refinement for dm16005 (yellow).

| | |
|---|---|
| Identification code | m16005/lt/B3401P021-yellow |
| Empirical formula | C3 H8 N2 Na O5 |
| Formula weight | 175.10 |
| Temperature | 100(2)K |
| Wavelength | 0.71073 Å |
| Crystal system | Monoclinic |
| Space group | $P2_1/c$ |
| Unit cell dimensions | a = 10.5000(10) Å  α = 90°. |
| | b = 52583(5) Å  β = 103.207(4)°. |
| | c = 13.0181(11) Å  γ = 90°. |
| Volume | 699.75(11) Å$^3$ |
| Z | 4 |
| Density (calculated) | 1.662 Mg/m$^3$ |
| Absorption coefficient | 0.204 mm$^{-1}$ |
| F(000) | 364 |
| Crystal size | 0.23 × 0.19 × 0.13 mm$^3$ |
| Theta range for data collection | 1.99 to 39.00°. |
| Index ranges | −18 ≤ h ≤ 17, −9 ≤ k ≤ 9, −22 ≤ l ≤ 23 |
| Reflections collected | 17310 |
| Independent reflections | 4040 [R(int) = 0.04] |
| Completeness to theta = 39.00° | 99.4% |
| Absorption correction | Semi-empirical from equivalents |
| Max. and min. transmission | 0.9739 and 0.9545 |
| Refinement method | Full-matrix least-squares on F$^2$ |
| Data/restraints/parameters | 4040/0/132 |
| Goodness-of-fit on F$^2$ | 1.045 |
| Final R indices [I > 2sigma(I)] | R1 = 0.0365, wR2 = 0.0924 |
| R indices (all data) | R1 = 0.0514, wR2 = 0.1005 |
| Largest diff. peak and hole | 0.744 and −0.309 e.Å$^{-3}$ |

TABLE 2Y

Atomic coordinates (×10$^4$) and equivalent isotropic displacement parameters (Å$^2$ × 10$^3$) for dm16005. U(eq) is defined as one third of the trace of the orthogonalized U$^{ij}$ tensor.

| | x | y | z | U(eq) |
|---|---|---|---|---|
| Na(1) | 5013(1) | 585(1) | 3712(1) | 10(1) |
| O(1) | 6904(1) | 3242(1) | 4474(1) | 11(1) |
| O(2) | 8116(1) | 5088(1) | 3474(1) | 13(1) |
| O(3) | 6108(1) | −1620(1) | 2599(1) | 11(1) |
| O(4) | 3129(1) | −2477(1) | 3412(1) | 14(1) |
| O(5) | 3823(1) | 2092(1) | 4915(1) | 11(1) |
| N(1) | 8824(1) | −4(1) | 5294(1) | 10(1) |
| N(2) | 9494(1) | −3201(2) | 6512(1) | 18(1) |
| C(1) | 7933(1) | 3462(1) | 4135(1) | 9(1) |
| C(2) | 9036(1) | 1636(1) | 4569(1) | 9(1) |
| C(3) | 9759(1) | −1648(1) | 5744(1) | 10(1) |

TABLE 3Y

Bond lengths [Å] and angles [°] for dm16005.

| | |
|---|---|
| Na(1)—O(3) | 2.3511(6) |
| Na(1)—O(5) | 2.3532(6) |
| Na(1)—O(3)#1 | 2.3533(7) |
| Na(1)—O(5)#2 | 2.3815(7) |
| Na(1)—O(1) | 2.4457(6) |
| Na(1)—O(4) | 2.5110(7) |
| Na(1)—Na(1)#2 | 3.4155(7) |
| Na(1)—Na(1)#3 | 4.1027(5) |
| Na(1)—Na(1)#1 | 4.1027(5) |
| O(1)—C(1) | 1.2618(8) |
| O(2)—C(1) | 1.2592(9) |
| O(3)—Na(1)#3 | 2.3534(7) |
| O(3)—H(3A) | 0.869(15) |
| O(3)—H(3B) | 0.823(15) |
| O(4)—H(4A) | 0.878(17) |
| O(4)—H(4B) | 0.827(17) |
| O(5)—Na(1)#2 | 2.3814(7) |
| O(5)—H(5A) | 0.874(16) |
| O(5)—H(5B) | 0.871(14) |
| N(1)—C(2) | 1.3339(9) |
| N(1)—C(3) | 1.3385(9) |
| N(2)—C(3) | 1.3687(10) |
| N(2)—H(2A) | 0.862(14) |
| N(2)—H(2B) | 0.891(14) |
| C(1)—C(2) | 1.5105(10) |
| C(2)—C(3)#4 | 1.4153(10) |
| C(3)—C(2)#4 | 1.4152(10) |
| O(3)—Na(1)—O(5) | 170.15(2) |
| O(3)—Na(1)—O(3)#1 | 95.449(17) |
| O(5)—Na(1)—O(3)#1 | 91.07(2) |
| O(3)—Na(1)—O(5)#2 | 86.08(2) |
| O(5)—Na(1)—O(5)#2 | 87.66(2) |
| O(3)#1—Na(1)—O(5)#2 | 177.57(2) |
| O(3)—Na(1)—O(1) | 93.75(2) |
| O(5)—Na(1)—O(1) | 92.47(2) |
| O(3)#1—Na(1)—O(1) | 99.33(2) |
| O(5)#2—Na(1)—O(1) | 78.66(2) |
| O(3)—Na(1)—O(4) | 93.84(2) |
| O(5)—Na(1)—O(4) | 78.47(2) |
| O(3)#1—Na(1)—O(4) | 92.42(2) |
| O(5)#2—Na(1)—O(4) | 89.36(2) |
| O(1)—Na(1)—O(4) | 165.33(2) |
| O(3)—Na(1)—Na(1)#2 | 129.13(2) |
| O(5)—Na(1)—Na(1)#2 | 44.160(16) |
| O(3)#1—Na(1)—Na(1)#2 | 135.20(2) |
| O(5)#2—Na(1)—Na(1)#2 | 43.502(15) |
| O(1)—Na(1)—Na(1)#2 | 83.835(18) |
| O(4)—Na(1)—Na(1)#2 | 81.636(18) |
| O(3)—Na(1)—Na(1)#3 | 29.317(15) |
| O(5)—Na(1)—Na(1)#3 | 144.77(2) |
| O(3)#1—Na(1)—Na(1)#3 | 85.888(19) |
| O(5)#2—Na(1)—Na(1)#3 | 96.338(17) |
| O(1)—Na(1)—Na(1)#3 | 122.678(18) |
| O(4)—Na(1)—Na(1)#3 | 66.623(15) |
| Na(1)#2—Na(1)—Na(1)#3 | 129.770(12) |

TABLE 3Y-continued

Bond lengths [Å] and angles [°] for dm16005.

| | |
|---|---|
| O(3)—Na(1)—Na(1)#1 | 76.118(19) |
| O(5)—Na(1)—Na(1)#1 | 112.639(17) |
| O(3)#1—Na(1)—Na(1)#1 | 29.285(14) |
| O(5)#2—Na(1)—Na(1)#1 | 150.22(2) |
| O(1)—Na(1)—Na(1)#1 | 78.905(15) |
| O(4)—Na(1)—Na(1)#1 | 115.15(2) |
| Na(1)#2—Na(1)—Na(1)#1 | 150.502(13) |
| Na(1)#3—Na(1)—Na(1)#1 | 79.709(13) |
| C(1)—O(1)—Na(1) | 126.28(5) |
| Na(1)—O(3)—Na(1)#3 | 121.40(3) |
| Na(1)—O(3)—H(3A) | 116.0(10) |
| Na(1)#3—O(3)—H(3A) | 102.3(10) |
| Na(1)—O(3)—H(3B) | 105.9(10) |
| Na(1)#3—O(3)—H(3B) | 105.7(10) |
| H(3A)—O(3)—H(3B) | 103.9(13) |
| Na(1)—O(4)—H(4A) | 98.7(11) |
| Na(1)—O(4)—H(4B) | 102.9(11) |
| H(4A)—O(4)—H(4B) | 109.9(14) |
| Na(1)—O(5)—Na(1)#2 | 92.34(2) |
| Na(1)—O(5)—H(5A) | 114.6(11) |
| Na(1)#2—O(5)—H(5A) | 97.3(10) |
| Na(1)—O(5)—H(5B) | 131.9(9) |
| Na(1)#2—O(5)—H(5B) | 111.0(9) |
| H(5A)—O(5)—H(5B) | 103.8(13) |
| C(2)—N(1)—C(3) | 120.18(6) |
| C(3)—N(2)—H(2A) | 119.5(9) |
| C(3)—N(2)—H(2B) | 117.4(9) |
| H(2A)—N(2)—H(2B) | 115.5(12) |
| O(2)—C(1)—O(1) | 125.27(7) |
| O(2)—C(1)—C(2) | 117.65(6) |
| O(1)—C(1)—C(2) | 117.08(6) |
| N(1)—C(2)—C(3)#4 | 120.73(6) |
| N(1)—C(2)—C(1) | 116.00(6) |
| C(3)#4—C(2)—C(1) | 123.27(6) |
| N(1)—C(3)—N(2) | 116.98(6) |
| N(1)—C(3)—C(2)#4 | 119.09(6) |
| N(2)—C(3)—C(2)#4 | 123.90(7) |

Symmetry transformations used to generate equivalent atoms:
1 −x + 1, y + ½, −z + ½
2 −x + 1, −y, −z + 1
3 −x + 1, y − ½, −z + ½
4 −x + 2, −y, −z + 1

TABLE 4Y

Anisotropic displacement parameters (Å$^2$ × 10$^3$) for dm16005.
The anisotropic displacement factor exponent takes the form:
$-2\pi^2[h^2 a^{*2} U^{11} + \ldots + 2 h k a^* b^* U^{12}]$

| | U$^{11}$ | U$^{22}$ | U$^{33}$ | U$^{23}$ | U$^{13}$ | U$^{12}$ |
|---|---|---|---|---|---|---|
| Na(1) | 10(1) | 11(1) | 11(1) | 0(1) | 3(1) | 1(1) |
| O(1) | 8(1) | 10(1) | 14(1) | 0(1) | 4(1) | 1(1) |
| O(2) | 12(1) | 13(1) | 15(1) | 5(1) | 4(1) | 3(1) |
| O(3) | 12(1) | 11(1) | 11(1) | 1(1) | 3(1) | 2(1) |
| O(4) | 17(1) | 14(1) | 12(1) | 0(1) | 5(1) | 2(1) |
| O(5) | 11(1) | 10(1) | 14(1) | −1(1) | 5(1) | 1(1) |
| N(1) | 8(1) | 10(1) | 12(1) | 2(1) | 3(1) | 2(1) |
| N(2) | 12(1) | 20(1) | 23(1) | 13(1) | 9(1) | 6(1) |
| C(1) | 8(1) | 9(1) | 10(1) | −1(1) | 1(1) | 1(1) |
| C(2) | 8(1) | 9(1) | 10(1) | 1(1) | 2(1) | 1(1) |
| C(3) | 9(1) | 11(1) | 12(1) | 2(1) | 4(1) | 1(1) |

TABLE 5Y

Hydrogen coordinates (×10$^4$) and isotropic displacement parameters (Å$^2$ × 10$^3$) for dm16005.

| | x | y | z | U(eq) |
|---|---|---|---|---|
| H(3A) | 6776(14) | −2530(30) | 2911(12) | 29(4) |
| H(3B) | 6428(13) | −520(30) | 2284(11) | 29(3) |
| H(4A) | 2538(16) | −1520(30) | 3001(14) | 40(4) |
| H(4B) | 2966(15) | −2590(30) | 4003(14) | 34(4) |
| H(5A) | 3053(15) | 1390(30) | 4852(13) | 36(4) |
| H(5B) | 3726(12) | 3610(30) | 5152(11) | 25(3) |
| H(2A) | 9998(13) | −4480(30) | 6728(11) | 22(3) |
| H(2B) | 8657(14) | −3410(30) | 6531(11) | 30(3) |

TABLE 6Y

Torsion angles [°] for dm16005.

| | |
|---|---|
| O(3)—Na(1)—O(1)—C(1) | 11.94(6) |
| O(5)—Na(1)—O(1)—C(1) | −175.71(6) |
| O(3)#1—Na(1)—O(1)—C(1) | −84.22(6) |
| O(5)#2—Na(1)—O(1)—C(1) | 97.17(6) |
| O(4)—Na(1)—O(1)—C(1) | 132.96(9) |
| Na(1)#2—Na(1)—O(1)—C(1) | 140.92(6) |
| Na(1)#3—Na(1)—O(1)—C(1) | 6.88(6) |
| Na(1)#1—Na(1)—O(1)—C(1) | −63.12(6) |
| O(5)—Na(1)—O(3)—Na(1)#3 | 59.71(15) |
| O(3)#1—Na(1)—O(3)—Na(1)#3 | −71.52(4) |
| O(5)#2—Na(1)—O(3)—Na(1)#3 | 110.37(3) |
| O(1)—Na(1)—O(3)—Na(1)#3 | −171.28(3) |
| O(4)—Na(1)—O(3)—Na(1)#3 | 21.28(3) |
| Na(1)#2—Na(1)—O(3)—Na(1)#3 | 103.62(3) |
| Na(1)#1—Na(1)—O(3)—Na(1)#3 | −93.69(3) |
| O(3)—Na(1)—O(5)—Na(1)#2 | 50.56(15) |
| O(3)#1—Na(1)—O(5)—Na(1)#2 | −177.93(2) |
| O(5)#2—Na(1)—O(5)—Na(1)#2 | 0.0 |
| O(1)—Na(1)—O(5)—Na(1)#2 | −78.54(2) |
| O(4)—Na(1)—O(5)—Na(1)#2 | 89.82(2) |
| Na(1)#3—Na(1)—O(5)—Na(1)#2 | 97.68(3) |
| Na(1)#1—Na(1)—O(5)—Na(1)#2 | −157.54(2) |
| Na(1)—O(1)—C(1)—O(2) | 90.49(8) |
| Na(1)—O(1)—C(1)—C(2) | −90.07(7) |
| C(3)—N(1)—C(2)—C(3)#4 | 0.69(12) |
| C(3)—N(1)—C(2)—C(1) | −178.18(6) |
| O(2)—C(1)—C(2)—N(1) | 177.82(6) |
| O(1)—C(1)—C(2)—N(1) | −1.66(9) |
| O(2)—C(1)—C(2)—C(3)#4 | −1.02(10) |
| O(1)—C(1)—C(2)—C(3)#4 | 179.50(7) |
| C(2)—N(1)—C(3)—N(2) | 177.38(7) |
| C(2)—N(1)—C(3)—C(2)#4 | −0.67(12) |

Symmetry transformations used to generate equivalent atoms:
1 −x + 1, y + ½, −z + ½
2 −x + 1, −y, −z + 1
3 −x + 1, y − ½, −z + ½
4 −x + 2, −y, −z + 1

TABLE 1R

Crystal data and structure refinement for dm16105.

| | |
|---|---|
| Identification code | m16105/lt/B3401P021-red |
| Empirical formula | $C_6 H_8 N_4 Na_2 O_6$ |
| Formula weight | 278.14 |
| Temperature | 100(2)K |
| Wavelength | 0.71073 Å |
| Crystal system | Monoclinic |
| Space group | C2/c |
| Unit cell dimensions | a = 20.549(6) Å  α = 90°. |
| | b = 3.5198(9) Å  β = 100.56(2)°. |
| | c = 13.289(4) Å  γ = 90°. |
| Volume | 944.9(5) Å$^3$ |
| Z | 4 |
| Density (calculated) | 1.955 Mg/m$^3$ |
| Absorption coefficient | 0.245 mm$^{-1}$ |
| F(000) | 568 |
| Crystal size | 0.15 × 0.08 × 0.03 mm$^3$ |
| Theta range for data collection | 2.02 to 23.29°. |
| Index ranges | −22 ≤ h ≤ 22, −3 ≤ k ≤ 3, −14 ≤ l ≤ 14 |

TABLE 1R-continued

Crystal data and structure refinement for dm16105.

| | |
|---|---|
| Reflections collected | 5401 |
| Independent reflections | 673 [R(int) = 0.11] |
| Completeness to theta = 23.29° | 99.9% |
| Absorption correction | None |
| Max. and min. transmission | 0.9927 and 0.9641 |
| Refinement method | Full-matrix least-squares on $F^2$ |
| Data/restraints/parameters | 673/1/94 |
| Goodness-of-fit on $F^2$ | 1.128 |
| Final R indices [I > 2sigma(I)] | R1 = 0.0656, wR2 = 0.1678 |
| R indices (all data) | R1 = 0.1011, wR2 = 0.1953 |
| Largest diff. peak and hole | 0.553 and −0.459 e.Å$^{-3}$ |

TABLE 2R

Atomic coordinates (×10$^4$) and equivalent isotropic displacement parameters (Å$^2$ × 10$^3$) for dm16105. U(eq) is defined as one third of the trace of the orthogonalized U$^{ij}$ tensor.

| | x | y | z | U(eq) |
|---|---|---|---|---|
| Na(1) | 0 | 4107(10) | −2500 | 18(1) |
| Na(2) | 2500 | 2500 | 0 | 18(1) |
| O(1) | 1044(2) | 5915(13) | −1625(3) | 18(1) |
| O(2) | 1697(2) | 7546(12) | −166(3) | 17(1) |
| O(3) | 2678(2) | 1457(16) | 1788(3) | 23(1) |
| N(1) | −24(2) | 8853(15) | −999(3) | 14(1) |
| N(2) | −1135(3) | 10283(16) | −1427(4) | 17(1) |
| C(1) | 1146(3) | 7295(18) | −736(5) | 14(2) |
| C(2) | 548(3) | 8715(18) | −334(5) | 14(1) |
| C(3) | −579(3) | 10076(18) | −695(4) | 14(1) |

TABLE 3R

Bond lengths [Å] and angles [°] for dm16105.

| | |
|---|---|
| Na(1)—O(1) | 2.334(4) |
| Na(1)—O(1)#1 | 2.334(4) |
| Na(1)—N(1) | 2.609(5) |
| Na(1)—N(1)#1 | 2.609(5) |
| Na(1)—N(1)#2 | 2.727(5) |
| Na(1)—N(1)#3 | 2.727(5) |
| Na(1)—Na(1)#3 | 3.5198(9) |
| Na(1)—Na(1)#4 | 3.5198(9) |
| Na(2)—O(3)#5 | 2.365(5) |
| Na(2)—O(3) | 2.365(5) |
| Na(2)—O(2)#6 | 2.383(4) |
| Na(2)—O(2)#3 | 2.383(4) |
| Na(2)—O(2)#5 | 2.407(4) |
| Na(2)—O(2) | 2.407(4) |
| Na(2)—Na(2)#3 | 3.5198(9) |
| Na(2)—Na(2)#4 | 3.5198(9) |
| Na(2)—H(3A) | 2.63(7) |
| O(1)—C(1) | 1.259(7) |
| O(2)—C(1) | 1.244(7) |
| O(2)—Na(2)#4 | 2.383(4) |
| O(3)—H(3A) | 0.96(8) |
| O(3)—H(3B) | 0.84(11) |
| N(1)—C(2) | 1.335(8) |
| N(1)—C(3) | 1.350(8) |
| N(1)—Na(1)#4 | 2.727(5) |
| N(2)—C(3) | 1.359(7) |
| N(2)—H(2A) | 0.87(4) |
| N(2)—H(2B) | 0.87(4) |
| C(1)—C(2) | 1.512(9) |
| C(2)—C(3)#7 | 1.422(9) |
| C(3)—C(2)#7 | 1.422(9) |
| O(1)—Na(1)—O(1)#1 | 148.4(3) |
| O(1)—Na(1)—N(1) | 65.72(16) |
| O(1)#1—Na(1)—N(1) | 93.56(17) |
| O(1)—Na(1)—N(1)#1 | 93.56(17) |
| O(1)#1—Na(1)—N(1)#1 | 65.72(16) |
| N(1)—Na(1)—N(1)#1 | 100.4(2) |
| O(1)—Na(1)—N(1)#2 | 114.29(16) |

TABLE 3R-continued

Bond lengths [Å] and angles [°] for dm16105.

| | |
|---|---|
| O(1)#1—Na(1)—N(1)#2 | 87.62(15) |
| N(1)—Na(1)—N(1)#2 | 177.1(2) |
| N(1)#1—Na(1)—N(1)#2 | 82.51(13) |
| O(1)—Na(1)—N(1)#3 | 87.62(15) |
| O(1)#1—Na(1)—N(1)#3 | 114.29(16) |
| N(1)—Na(1)—N(1)#3 | 82.51(13) |
| N(1)#1—Na(1)—N(1)#3 | 177.1(2) |
| N(1)#2—Na(1)—N(1)#3 | 94.6(2) |
| O(1)—Na(1)—Na(1)#3 | 105.83(14) |
| O(1)#1—Na(1)—Na(1)#3 | 105.82(14) |
| N(1)—Na(1)—Na(1)#3 | 129.81(12) |
| N(1)#1—Na(1)—Na(1)#3 | 129.81(12) |
| N(1)#2—Na(1)—Na(1)#3 | 47.30(12) |
| N(1)#3—Na(1)—Na(1)#3 | 47.30(12) |
| O(1)—Na(1)—Na(1)#4 | 74.18(14) |
| O(1)#1—Na(1)—Na(1)#4 | 74.17(14) |
| N(1)—Na(1)—Na(1)#4 | 50.19(12) |
| N(1)#1—Na(1)—Na(1)#4 | 50.19(12) |
| N(1)#2—Na(1)—Na(1)#4 | 132.70(12) |
| N(1)#3—Na(1)—Na(1)#4 | 132.70(12) |
| Na(1)#3—Na(1)—Na(1)#4 | 179.998(1) |
| O(3)#5—Na(2)—O(3) | 180.0 |
| O(3)#5—Na(2)—O(2)#6 | 87.51(15) |
| O(3)—Na(2)—O(2)#6 | 92.49(15) |
| O(3)#5—Na(2)—O(2)#3 | 92.49(15) |
| O(3)—Na(2)—O(2)#3 | 87.51(15) |
| O(2)#6—Na(2)—O(2)#3 | 180.0 |
| O(3)#5—Na(2)—O(2)#5 | 100.60(16) |
| O(3)—Na(2)—O(2)#5 | 79.40(16) |
| O(2)#6—Na(2)—O(2)#5 | 94.58(14) |
| O(2)#3—Na(2)—O(2)#5 | 85.42(14) |
| O(3)#5—Na(2)—O(2) | 79.40(16) |
| O(3)—Na(2)—O(2) | 100.60(16) |
| O(2)#6—Na(2)—O(2) | 85.42(14) |
| O(2)#3—Na(2)—O(2) | 94.58(14) |
| O(2)#5—Na(2)—O(2) | 180.0 |
| O(3)#5—Na(2)—Na(2)#3 | 98.93(14) |
| O(3)—Na(2)—Na(2)#3 | 81.07(14) |
| O(2)#6—Na(2)—Na(2)#3 | 137.03(10) |
| O(2)#3—Na(2)—Na(2)#3 | 42.97(10) |
| O(2)#5—Na(2)—Na(2)#3 | 42.45(10) |
| O(2)—Na(2)—Na(2)#3 | 137.55(10) |
| O(3)#5—Na(2)—Na(2)#4 | 81.07(14) |
| O(3)—Na(2)—Na(2)#4 | 98.93(14) |
| O(2)#6—Na(2)—Na(2)#4 | 42.97(10) |
| O(2)#3—Na(2)—Na(2)#4 | 137.02(10) |
| O(2)#5—Na(2)—Na(2)#4 | 137.56(10) |
| O(2)—Na(2)—Na(2)#4 | 42.45(10) |
| Na(2)#3—Na(2)—Na(2)#4 | 180.0 |
| O(3)#5—Na(2)—H(3A) | 158.6(17) |
| O(3)—Na(2)—H(3A) | 21.4(17) |
| O(2)#6—Na(2)—H(3A) | 79.2(18) |
| O(2)#3—Na(2)—H(3A) | 100.8(18) |
| O(2)#5—Na(2)—H(3A) | 64.3(18) |
| O(2)—Na(2)—H(3A) | 115.7(18) |
| Na(2)#3—Na(2)—H(3A) | 80.3(18) |
| Na(2)#4—Na(2)—H(3A) | 99.7(18) |
| C(1)—O(1)—Na(1) | 123.5(4) |
| C(1)—O(2)—Na(2)#4 | 130.2(4) |
| C(1)—O(2)—Na(2) | 122.4(4) |
| Na(2)#4—O(2)—Na(2) | 94.58(14) |
| Na(2)—O(3)—H(3A) | 95(4) |
| Na(2)—O(3)—H(3B) | 125(7) |
| H(3A)—O(3)—H(3B) | 99(8) |
| C(2)—N(1)—C(3) | 120.2(5) |
| C(2)—N(1)—Na(1) | 110.2(4) |
| C(3)—N(1)—Na(1) | 124.6(4) |
| C(2)—N(1)—Na(1)#4 | 112.2(4) |
| C(3)—N(1)—Na(1)#4 | 97.6(4) |
| Na(1)—N(1)—Na(1)#4 | 82.51(13) |
| C(3)—N(2)—H(2A) | 114(4) |
| C(3)—N(2)—H(2B) | 118(4) |
| H(2A)—N(2)—H(2B) | 123(6) |
| O(2)—C(1)—O(1) | 125.1(6) |
| O(2)—C(1)—C(2) | 118.0(5) |
| O(1)—C(1)—C(2) | 116.9(5) |
| N(1)—C(2)—C(3)#7 | 120.4(6) |
| N(1)—C(2)—C(1) | 116.9(5) |

TABLE 3R-continued

Bond lengths [Å] and angles [°] for dm16105.

| | |
|---|---|
| C(3)#7—C(2)—C(1) | 122.8(5) |
| N(1)—C(3)—N(2) | 116.7(5) |
| N(1)—C(3)—C(2)#7 | 119.4(5) |
| N(2)—C(3)—C(2)#7 | 123.8(6) |

Symmetry transformations used to generate equivalent atoms:
1 −x, y, −z − ½
2 −x, y − 1, −z − ½
3 x, y − 1, z
4 x, y + 1, z
5 −x + ½, −y + ½, −z
6 −x + ½, −y + 3/2, −z
7 −x, −y + 2, −z

TABLE 4R

Anisotropic displacement parameters (Å$^2$ × 10$^3$) for dm16105.
The anisotropic displacement factor exponent takes the form:
−2π$^2$[h$^2$ a*$^2$U$^{11}$ + ... + 2 h k a* b* U$^{12}$]

| | U$^{11}$ | U$^{22}$ | U$^{33}$ | U$^{23}$ | U$^{13}$ | U$^{12}$ |
|---|---|---|---|---|---|---|
| Na(1) | 23(2) | 12(2) | 19(2) | 0 | 3(1) | 0 |
| Na(2) | 19(2) | 12(2) | 24(2) | 2(2) | 5(2) | −1(2) |
| O(1) | 21(2) | 16(3) | 17(2) | −3(2) | 3(2) | 1(2) |
| O(2) | 20(3) | 9(3) | 22(2) | 0(2) | 2(2) | 2(2) |
| O(3) | 20(3) | 25(3) | 25(3) | −1(2) | 7(2) | −2(2) |
| N(1) | 17(3) | 2(3) | 22(3) | 0(2) | 4(2) | −1(2) |
| N(2) | 20(3) | 13(4) | 19(3) | −4(3) | 4(3) | 3(3) |
| C(1) | 16(4) | 2(4) | 22(4) | 5(3) | 3(3) | −2(3) |
| C(2) | 19(3) | 3(3) | 20(2) | 5(2) | 1(2) | −1(2) |
| C(3) | 19(3) | 3(3) | 20(2) | 5(2) | 1(2) | −1(2) |

TABLE 5R

Hydrogen coordinates (×10$^4$) and isotropic displacement parameters (Å$^2$ × 10$^3$) for dm16105.

| | x | y | z | U(eq) |
|---|---|---|---|---|
| H(3A) | 3150(40) | 1200(200) | 1860(50) | 40(20) |
| H(3B) | 2660(50) | 3100(300) | 2230(70) | 80(40) |
| H(2A) | −1120(30) | 8900(170) | −1960(40) | 14(17) |
| H(2B) | −1510(20) | 10860(180) | −1240(40) | 10(16) |

TABLE 6R

Torsion angles [°] for dm16105.

| | |
|---|---|
| O(1)#1—Na(1)—O(1)—C(1) | 72.9(5) |
| N(1)—Na(1)—O(1)—C(1) | 20.0(5) |
| N(1)#1—Na(1)—O(1)—C(1) | 119.8(5) |
| N(1)#2—Na(1)—O(1)—C(1) | −156.9(5) |
| N(1)#3—Na(1)—O(1)—C(1) | −62.9(5) |
| Na(1)#3—Na(1)—O(1)—C(1) | −107.1(5) |
| Na(1)#4—Na(1)—O(1)—C(1) | 72.9(5) |
| O(3)#5—Na(2)—O(2)—C(1) | 56.5(4) |
| O(3)—Na(2)—O(2)—C(1) | −123.5(4) |
| O(2)#6—Na(2)—O(2)—C(1) | 144.8(5) |
| O(2)#3—Na(2)—O(2)—C(1) | −35.2(5) |
| O(2)#5—Na(2)—O(2)—C(1) | 8(7) |
| Na(2)#3—Na(2)—O(2)—C(1) | −35.2(5) |
| Na(2)#4—Na(2)—O(2)—C(1) | 144.8(5) |
| O(3)#5—Na(2)—O(2)—Na(2)#4 | −88.32(16) |
| O(3)—Na(2)—O(2)—Na(2)#4 | 91.68(16) |
| O(2)#6—Na(2)—O(2)—Na(2)#4 | 0.0 |
| O(2)#3—Na(2)—O(2)—Na(2)#4 | 180.0 |
| O(2)#5—Na(2)—O(2)—Na(2)#4 | −137(6) |
| Na(2)#3—Na(2)—O(2)—Na(2)#4 | 180.0 |
| O(1)—Na(1)—N(1)—C(2) | −21.7(4) |
| O(1)#1—Na(1)—N(1)—C(2) | −176.9(4) |
| N(1)#1—Na(1)—N(1)—C(2) | −110.9(4) |

TABLE 6R-continued

Torsion angles [°] for dm16105.

| | |
|---|---|
| N(1)#2—Na(1)—N(1)—C(2) | 69.1(4) |
| N(1)#3—Na(1)—N(1)—C(2) | 69.1(4) |
| Na(1)#3—Na(1)—N(1)—C(2) | 69.1(4) |
| Na(1)#4—Na(1)—N(1)—C(2) | −110.9(4) |
| O(1)—Na(1)—N(1)—C(3) | −176.7(5) |
| O(1)#1—Na(1)—N(1)—C(3) | 28.1(5) |
| N(1)#1—Na(1)—N(1)—C(3) | 94.1(5) |
| N(1)#2—Na(1)—N(1)—C(3) | −85.9(5) |
| N(1)#3—Na(1)—N(1)—C(3) | −85.9(5) |
| Na(1)#3—Na(1)—N(1)—C(3) | −85.9(5) |
| Na(1)#4—Na(1)—N(1)—C(3) | 94.1(5) |
| O(1)—Na(1)—N(1)—Na(1)#4 | 89.24(16) |
| O(1)#1—Na(1)—N(1)—Na(1)#4 | −65.95(15) |
| N(1)#1—Na(1)—N(1)—Na(1)#4 | 0.002(1) |
| N(1)#2—Na(1)—N(1)—Na(1)#4 | 179.998(11) |
| N(1)#3 —Na(1)—N(1)—Na(1)#4 | 180.0 |
| Na(1)#3—Na(1)—N(1)—Na(1)#4 | 180.0 |
| Na(2)#4—O(2)—C(1)—O(1) | 89.2(7) |
| Na(2)—O(2)—C(1)—O(1) | −42.1(8) |
| Na(2)#4—O(2)—C(1)—C(2) | −91.4(6) |
| Na(2)—O(2)—C(1)—C(2) | 137.3(5) |
| Na(1)—O(1)—C(1)—O(2) | 164.0(5) |
| Na(1)—O(1)—C(1)—C(2) | −15.3(8) |
| C(3)—N(1)—C(2)—C(3)#7 | −1.2(10) |
| Na(1)—N(1)—C(2)—C(3)#7 | −157.5(5) |
| Na(1)#4—N(1)—C(2)—C(3)#7 | 112.5(5) |
| C(3)—N(1)—C(2)—C(1) | 179.8(5) |
| Na(1)—N(1)—C(2)—C(1) | 23.5(7) |
| Na(1)#4 —N(1)—C(2)—C(1) | −66.5(6) |
| O(2)—C(1)—C(2)—N(1) | 172.0(5) |
| O(1)—C(1)—C(2)—N(1) | −8.6(9) |
| O(2)—C(1)—C(2)—C(3)#7 | −7.0(9) |
| O(1)—C(1)—C(2)—C(3)#7 | 172.4(6) |
| C(2)—N(1)—C(3)—N(2) | 177.4(5) |
| Na(1)—N(1)—C(3)—N(2) | −30.0(8) |
| Na(1)#4—N(1)—C(3)—N(2) | 56.1(6) |
| C(2)—N(1)—C(3)—C(2)#7 | 1.2(10) |
| Na(1)—N(1)—C(3)—C(2)#7 | 153.9(4) |
| Na(1)#4—N(1)—C(3)—C(2)#7 | −120.0(5) |

Symmetry transformations used to generate equivalent atoms:
1 −x, y, −z − ½
2 −x, y − 1, −z − ½
3 x, y − 1, z
4 x, y + 1, z
5 −x + ½, −y + ½, −z
6 −x + ½, −y + 3/2, −z
7 −x, −y + 2, −z Various publications are referenced throughout this disclosure by Arabic numerals in brackets. A full citation corresponding to each reference number is listed below. The disclosures of these publications are herein incorporated by reference in their entireties.

REFERENCES

1. Nally, J. V. Acute renal failure in hospitalized patients. *Cleveland Clinic Journal of Medicine* 2002, 69(7), 569-574.

2. C. A. Rabito, L. S. T. Fang, and A. C. Waltman. Renal function in patients at risk with contrast material-induced acute renal failure: Noninvasive real-time monitoring. *Radiology* 1993, 186, 851-854.

3. N. L. Tilney, and J. M. Lazarus. Acute renal failure in surgical patients: Causes, clinical patterns, and care. *Surgical Clinics of North America* 1983, 63, 357-377.

4. B. E. VanZee, W. E. Hoy, and J. R. Jaenike. Renal injury associated with intravenous pyelography in non-diabetic and diabetic patients. *Annals of Internal Medicine* 1978, 89, 51-54.

5. S. Lundqvist, G. Edbom, S. Groth, U. Stendahl, and S.-O. Hietala. Iohexyl clearance for renal function measurement in gynecologic cancer patients. *Acta Radiologica* 1996, 37, 582-586.
6. P. Guesry, L. Kaufman, S. Orloff, J. A. Nelson, S. Swann, and M. Holliday. Measurement of glomerular filtration rate by fluorescent excitation of non-radioactive meglumine iothalamate. *Clinical Nephrology* 1975, 3, 134-138).
7. C. C. Baker et al. Epidemiology of Trauma Deaths. *American Journal of Surgery* 1980, 144-150.
8. R. G. Lobenhoffer et al. Treatment Results of Patients with Multiple Trauma: An Analysis of 3406 Cases Treated Between 1972 and 1991 at a German Level I Trauma Center. *Journal of Trauma* 1995, 38, 70-77.
9. J. Coalson, Pathology of Sepsis, Septic Shock, and Multiple Organ Failure. In *New Horizons: Multiple Organ Failure*, D. J. Bihari and F. B. Cerra, (Eds). Society of Critical Care Medicine, Fullerton, Calif., 1986, pp. 27-59.
10. F. B. Cerra, Multiple Organ Failure Syndrome. In *New Horizons: Multiple Organ Failure*, D. J. Bihari and F. B. Cerra, (Eds). Society of Critical Care Medicine, Fullerton, Calif., 1989, pp. 1-24.
11. R. Muller-Suur, and C. Muller-Suur. Glomerular filtration and tubular secretion of $MAG_3$ in rat kidney. *Journal of Nuclear Medicine* 1989, 30, 1986-1991).
12. P. D. Dollan, E. L. Alpen, and G. B. Theil. A clinical appraisal of the plasma concentration and endogenous clearance of creatinine. *American Journal of Medicine* 1962, 32, 65-79.
13. J. B. Henry (Ed). *Clinical Diagnosis and Management by Laboratory Methods*, 17th Edition, W.B. Saunders, Philadelphia, Pa., 1984.
14. F. Roch-Ramel, K. Besseghir, and H. Murer. Renal excretion and tubular transport of organic anions and cations. In *Handbook of Physiology, Section 8, Neurological Physiology, Vol. II*, E. E. Windhager, Editor, pp. 2189-2262. Oxford University Press: New York, 1992
15. D. L. Nosco and J. A. Beaty-Nosco. Chemistry of technetium radiopharmaceuticals 1: Chemistry behind the development of technetium-99m compounds to determine kidney function. *Coordination Chemistry Reviews* 1999, 184, 91-123.
16. P. L. Choyke, H. A. Austin, and J. A. Frank. Hydrated clearance of gadolinium-DTPA as a measurement of glomerular filtration rate. *Kidney International* 1992, 41, 1595-1598.
17. N. Lewis, R. Kerr, and C. Van Buren. Comparative evaluation of urographic contrast media, inulin, and $^{99m}$Tc-DTPA clearance methods for determination of glomerular filtration rate in clinical transplantation. *Transplantation* 1989, 48, 790-796).
18. W. N. Tauxe. Tubular Function. In *Nuclear Medicine in Clinical Urology and Nephrology*, W. N. Tauxe and E. V. Dubovsky, Editors, pp. 77-105, Appleton Century Crofts: East Norwalk, 1985.
19. A. R. Fritzberg et al. Mercaptoacetylglycylglycyglycine. *Journal of Nuclear Medicine* 1986, 27, 111-120.
20. G. Ekanoyan and N. W. Levin. In *Clinical Practice Guidelines for Chronic Kidney Disease: Evaluation, Classification, and Stratification (K/DOQI)*. National Kidney Foundation: Washington, D.C. 2002, pp. 1-22.
21. Ozaki, H. et al. Sensitization of europium(III) luminescence by DTPA derivatives. *Chemistry Letters* 2000, 312-313.
22. Rabito, C. Fluorescent agents for real-time measurement of organ function. U.S. Pat. No. 6,440,389; 2002.
23. R. Rajagopalan, R. et al. Polyionic fluorescent bioconjugates as composition agents for continuous monitoring of renal function. In *Molecular Imaging: Reporters, Dyes, Markers, and Instrumentation*, A. Priezzhev, T. Asakura, and J. D. Briers, Editors, Proceedings of SPIE, 2000, 3924.
24. Dorshow, R. B. et al. Noninvasive renal function assessment by fluorescence detection. In *Biomedical Optical Spectroscopy and Diagnostics, Trends in Optics and Photonics Series* 22, E. M Sevick-Muraca, J. A. Izatt, and M. N. Ediger, Editors, pp. 54-56, Optical Society of America, Washington D.C., 1998.
25. Shirai, K. et al Synthesis and fluorescent properties of 2,5-diamino-3,6-dicyanopyrazine dyes. *Dyes and Pigments* 1998, 39(1), 49-68.
26. Kim, J. H. et al. Self-assembling of aminopyrazine fluorescent dyes and their solid state spectra. *Dyes and Pigments* 1998, 39(4), 341-357.
27. Barlin, G. B. The pyrazines. In The Chemistry of Heterocyclic Compounds. A. Weissberger and E. C. Taylor, Eds. John Wiley & Sons, New York: 1982.
28. Donald, D. S. Synthesis of 3,5-diaminopyrazinoic acid from 3,5-diamino-2,6-dicyanopyrazine and intermediates. U.S. Pat. No. 3,948,895; 1976.
29. Donald, D. S. Diaminosubstituted dicyanopyrzines and process. U.S. Pat. No. 3,814,757; 1974.
30. Muller et al. Eds, *Medical Optical Tomography*, SPIE Volume IS11, 1993.
31. R. B. Dorshow et al. Non-Invasive Fluorescence Detection of Hepatic and Renal Function, *Bull. Am. Phys. Soc.* 1997, 42, 681.
32. R. B. Dorshow et al. Monitoring Physiological Function by Detection of Exogenous Fluorescent Contrast Agents. In *Optical Diagnostics of Biological Fluids IV*, A. Priezzhev and T. Asakura, Editors, Proceedings of SPIE 1999, 3599, 2-8).

What is claimed is:

1. A compound of Formula I wherein:

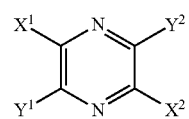

Formula I each of $X^1$ and $X^2$ is independently selected from the group consisting of —CN, —$CO_2R^1$, —$CONR^2R^3$, —$COR^4$, —$SOR^5$, —$SO_2R^6$, —$SO_2OR^7$ and —$PO_3R^8R^9$;
each of $Y^1$ and $Y^2$ is independently selected from the group consisting of —$OR^{10}$, —$SR^{11}$, —$NR^{12}R^{13}$, —$N(R^{14})COR^{15}$ and

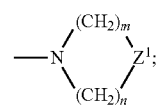

$Z^1$ is selected from the group consisting of a direct bond, —$CR^{16}R^{17}$—, —O—, —$NR^{18}$—, —$NCOR^{19}$—, —S—, —SO— and —$SO_2$—;
each of $R^1$ to $R^9$, $R^{11}$, and $R^{16}$ to $R^{19}$ is independently selected from the group consisting of hydrogen, C3-C6 polyhydroxylated alkyl, —$((CH_2)_2$—O—$(CH_2)_2$—

O)$_a$—R$^{40}$, C1-C10 alkyl, C5-C10 aryl, C5-C10 heteroaryl, —(CH$_2$)$_a$OH, —(CH$_2$)$_a$CO$_2$H, —(CH$_2$)$_a$SO$_3$H, —(CH$_2$)$_a$SO$_3^-$, —(CH$_2$)$_a$OSO$_3$H, —(CH$_2$)$_a$OSO$_3^-$, —(CH$_2$)$_a$NHSO$_3$H, —(CH$_2$)$_a$NHSO$_3^-$, —(CH$_2$)$_a$PO$_3$H$_2$, —(CH$_2$)$_a$PO$_3$H$^-$, —(CH$_2$)$_a$PO$_3^=$, —(CH$_2$)$_a$OPO$_3$H$_2$, —(CH$_2$)$_a$OPO$_3$H$^-$ and —(CH$_2$)$_a$OPO$_3$;

each of R$^{12}$ to R$^{15}$ is independently selected from the group consisting of hydrogen, C3-C6 polyhydroxylated alkyl, —((CH$_2$)$_2$—O—(CH$_2$)$_2$—O)$_a$—R$^{40}$, —(CH$_2$)$_a$OH, —(CH$_2$)$_a$CO$_2$H, —(CH$_2$)$_a$SO$_3$H, —(CH$_2$)$_a$SO$_3^-$, —(CH$_2$)$_a$OSO$_3$H, —(CH$_2$)$_a$OSO$_3^-$, —(CH$_2$)$_a$NHSO$_3$H, —(CH$_2$)$_a$NHSO$_3^-$, —(CH$_2$)$_a$PO$_3$H$_2$, —(CH$_2$)$_a$PO$_3$H$^-$, —(CH$_2$)$_a$PO$_3^=$, —(CH$_2$)$_a$OPO$_3$H$_2$, —(CH$_2$)$_a$OPO$_3$H$^-$ and —(CH$_2$)$_a$OPO$_3$;

R$^{10}$ is selected from the group consisting of C3-C6 polyhydroxylated alkyl, —((CH$_2$)$_2$—O—(CH$_2$)$_2$—O)$_a$—R$^{40}$, C1-C10 alkyl, C5-C10 aryl, C5-C10 heteroaryl, —(CH$_2$)$_a$OH, —(CH$_2$)$_a$CO$_2$H, —(CH$_2$)$_a$SO$_3$H, —(CH$_2$)$_a$SO$_3^-$, —(CH$_2$)$_a$OSO$_3$H, —(CH$_2$)$_a$OSO$_3^-$, —(CH$_2$)$_a$NHSO$_3$H, —(CH$_2$)$_a$NHSO$_3^-$, —(CH$_2$)$_a$PO$_3$H$_2$, —(CH$_2$)$_a$PO$_3$H$^-$, —(CH$_2$)$_a$PO$_3^=$, —(CH$_2$)$_a$OPO$_3$H$_2$, —(CH$_2$)$_a$OPO$_3$H$^-$ and —(CH$_2$)$_a$OPO$_3$;

R$^{40}$ is selected from the group consisting of hydrogen, C1-C10 alkyl, C5-C10 aryl, C5-C10 heteroaryl, —(CH$_2$)$_a$OH, —(CH$_2$)$_a$CO$_2$H, —(CH$_2$)$_a$SO$_3$H, —(CH$_2$)$_a$SO$_3^-$, —(CH$_2$)$_a$OSO$_3$H, —(CH$_2$)$_a$OSO$_3^-$, —(CH$_2$)$_a$NHSO$_3$H, —(CH$_2$)$_a$NHSO$_3^-$, —(CH$_2$)$_a$PO$_3$H$_2$, —(CH$_2$)$_a$PO$_3$H$^-$, —(CH$_2$)$_a$PO$_3^=$, —(CH$_2$)$_a$OPO$_3$H$_2$, —(CH$_2$)$_a$OPO$_3$H$^-$ and —(CH$_2$)$_a$OPO$_3$; and each of a, m and n range from 1 to 6;

with the proviso that if:

each of X$^1$ and X$^2$ is independently —CN, —CO$_2$R$^1$ or —CONR$^2$R$^3$;

each of Y$^1$ and Y$^2$ is independently —NR$^{12}$R$^{13}$ or

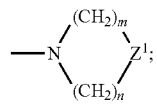

and

Z$^1$ is a direct bond, then:

each of R$^1$, R$^2$, R$^3$, R$^{12}$ and R$^{13}$ is independently not hydrogen, C1-C10 alkyl or C1-C10 aryl; and the sum of m and n is not 4 or 5.

2. The compound of claim 1 wherein:

each of X$^1$ and X$^2$ is independently selected from the group consisting of —CN, —CO$_2$R$^1$ and —CONR$^2$R$^3$;

each of Y$^1$ and Y$^2$ is independently —NR$^{12}$R$^{13}$ or

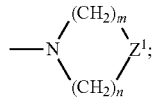

each of R$^1$, R$^2$, R$^3$, R$^{12}$ and R$^{13}$ is independently selected from the group consisting of C3-C6 polyhydroxylated alkyl, —((CH$_2$)$_2$—O—(CH$_2$)$_2$—O)$_a$—R$^{40}$, —(CH$_2$)$_a$OH, —(CH$_2$)$_a$CO$_2$H, —(CH$_2$)$_a$SO$_3$H and —(CH$_2$)$_a$SO$_3^-$;

each of R$^{16}$ to R$^{19}$ is independently selected from the group consisting of hydrogen, C3-C6 polyhydroxylated alkyl, —((CH$_2$)$_2$—O—(CH$_2$)$_2$—O)$_a$—R$^{40}$, C1-C10 alkyl, C5-C10 aryl, C5-C10 heteroaryl, —(CH$_2$)$_a$OH, —(CH$_2$)$_a$CO$_2$H, —(CH$_2$)$_a$SO$_3$H and —(CH$_2$)$_a$SO$_3^-$;

m is 1 or 2; and n is 1.

3. The compound of claim 2 wherein:

each of X$^1$ and X$^2$ is —CN;

each of Y$^1$ and Y$^2$ is independently selected from the group consisting of —NR$^{12}$R$^{13}$ and

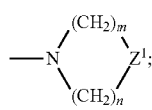

Z$^1$ is selected from the group consisting of a direct bond, —O—, —NR$^{18}$—, —NCOR$^{19}$—, —S—, —SO— and —SO$_2$—;

each of R$^{12}$ and R$^{13}$ is independently selected from the group consisting of C3-C6 polyhydroxylated alkyl, —((CH$_2$)$_2$—O—(CH$_2$)$_2$—O)$_a$—R$^{40}$, —(CH$_2$)$_a$OH, —(CH$_2$)$_a$CO$_2$H, —(CH$_2$)$_a$SO$_3$H and —(CH$_2$)$_a$SO$_3^-$;

each of R$^{18}$ and R$^{19}$ is independently selected from the group consisting of hydrogen, C3-C6 polyhydroxylated alkyl, —((CH$_2$)$_2$—O—(CH$_2$)$_2$—O)$_a$—R$^{40}$, C1-C10 alkyl, —(CH$_2$)$_a$OH, —(CH$_2$)$_a$CO$_2$H, —(CH$_2$)$_a$SO$_3$H and —(CH$_2$)$_a$SO$_3^-$;

m is 1 or 2; and n is 1.

4. The compound of claim 3 wherein:

each of Y$^1$ and Y$^2$ is —NR$^{12}$R$^{13}$; and each of R$^{12}$ and R$^{13}$ is —(CH$_2$)$_a$CO$_2$H.

5. The compound of claim 3 wherein:

each of Y$^1$ and Y$^2$ is

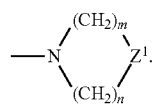

6. The compound of claim 2 wherein:

each of X$^1$ and X$^2$ is —CO$_2$R$^1$;

each of Y$^1$ and Y$^2$ is independently selected from the group consisting of —NR$^{12}$R$^{13}$ and

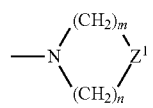

Z$^1$ is selected from the group consisting of a direct bond, —O—, —NR$^{18}$—, —NCOR$^{19}$—, —S—, —SO— and —SO$_2$—;

each of R$^{12}$ and R$^{13}$ is independently selected from the group consisting of C3-C6 polyhydroxylated alkyl, —((CH$_2$)$_2$—O—(CH$_2$)$_2$—O)$_a$—R$^{40}$, —(CH$_2$)$_a$OH, —(CH$_2$)$_a$CO$_2$H, —(CH$_2$)$_a$SO$_3$H and —(CH$_2$)$_a$SO$_3^-$; and each of R$^{18}$ and R$^{19}$ is independently selected from the group consisting of hydrogen, C3-C6 polyhydroxylated alkyl, $-((CH_2)_2-O-(CH_2)_2-O)_a-R^{40}$, C1-C10 alkyl, $-(CH_2)_aOH$, $-(CH_2)_aCO_2H$, $-(CH_2)_aSO_3H$ and $-(CH_2)_aSO_3^-$.
7. The compound of claim 6 wherein:
each of $Y^1$ and $Y^2$ is $-NR^{12}R^{13}$; and
each of $R^{12}$ and $R^{13}$ is $-(CH_2)_aCO_2H$.
8. The compound of claim 6 wherein:
each of $Y^1$ and $Y^2$ is
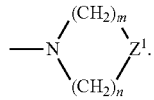
* * * * *